(12) United States Patent
Kahn et al.

(10) Patent No.: US 9,144,398 B1
(45) Date of Patent: Sep. 29, 2015

(54) SENSOR FUSION FOR ACTIVITY IDENTIFICATION

(71) Applicants: Philippe Richard Kahn, Santa Cruz, CA (US); Arthur Kinsolving, Santa Cruz, CA (US); Mark Andrew Christensen, Santa Cruz, CA (US); Brian Y. Lee, Santa Cruz, CA (US); David Vogel, Santa Cruz, CA (US)

(72) Inventors: Philippe Richard Kahn, Santa Cruz, CA (US); Arthur Kinsolving, Santa Cruz, CA (US); Mark Andrew Christensen, Santa Cruz, CA (US); Brian Y. Lee, Santa Cruz, CA (US); David Vogel, Santa Cruz, CA (US)

(73) Assignee: DP Technologies, Inc., Scotts Valley, CA (US)

( * ) Notice: Subject to any disclaimer, the term of this patent is extended or adjusted under 35 U.S.C. 154(b) by 0 days.

(21) Appl. No.: 14/338,339

(22) Filed: Jul. 22, 2014

Related U.S. Application Data

(60) Continuation of application No. 14/061,701, filed on Oct. 23, 2013, now Pat. No. 8,784,309, which is a continuation of application No. 13/476,962, filed on May 21, 2012, now Pat. No. 8,568,310, which is a division of application No. 12/202,206, filed on Aug. 29, 2008, now Pat. No. 8,187,182.

(51) Int. Cl.
*A63B 24/00* (2006.01)
*A61B 5/11* (2006.01)
*A61B 5/00* (2006.01)

(52) U.S. Cl.
CPC ............. *A61B 5/1118* (2013.01); *A61B 5/1112* (2013.01); *A61B 5/4866* (2013.01); *A61B 5/6898* (2013.01); *A61B 5/7221* (2013.01); *A61B 5/7278* (2013.01)

(58) Field of Classification Search
CPC .. A61B 5/1118; A61B 5/1112; A61B 5/6898; A61B 5/4866; A61B 5/7278; A61B 5/7221; A63B 24/00
USPC .......... 482/1–9, 900–902; 340/573.1; 600/300
See application file for complete search history.

(56) References Cited

U.S. PATENT DOCUMENTS

| | | | |
|---|---|---|---|
| 4,285,041 A | 8/1981 | Smith |
| 4,571,680 A | 2/1986 | Wu |
| 4,578,769 A | 3/1986 | Frederick |
| 5,446,725 A | 8/1995 | Ishiwatari |

(Continued)

FOREIGN PATENT DOCUMENTS

WO    WO 01/88477 A2    11/2001

OTHER PUBLICATIONS

Anderson, Ian, et al, "Shakra: Tracking and Sharing Daily Activity Levels with Unaugmented Mobile Phones," Mobile Netw Appl, Aug. 3, 2007, pp. 185-199.

(Continued)

*Primary Examiner* — Glenn Richman
(74) *Attorney, Agent, or Firm* — HIPLegal LLP; Judith A. Szepesi

(57) ABSTRACT

An mobile device to monitor human activity using multiple sensors comprising a processing unit to provide a first estimation user activity data based on data from a first sensor, the first estimation having a first accuracy estimation, and to provide a second estimation of user activity data based on data from a second sensor, the second estimation having a second accuracy estimation, and the processor to calculate the user activity statistic based on the first estimation and the second estimation, wherein the calculated user activity statistic is a result of a weighted combination of the first estimation and the second estimation.

20 Claims, 11 Drawing Sheets

(56) References Cited

U.S. PATENT DOCUMENTS

| | | |
|---|---|---|
| 5,446,775 A | 8/1995 | Wright et al. |
| 5,583,776 A | 12/1996 | Levi et al. |
| 5,593,431 A | 1/1997 | Sheldon |
| 5,654,619 A | 8/1997 | Iwashita |
| 5,778,882 A | 7/1998 | Raymond et al. |
| 5,955,667 A | 9/1999 | Fyfe |
| 5,976,083 A | 11/1999 | Richardson et al. |
| 6,013,007 A | 1/2000 | Root et al. |
| 6,122,595 A | 9/2000 | Varley et al. |
| 6,135,951 A | 10/2000 | Richardson et al. |
| 6,145,389 A | 11/2000 | Ebeling et al. |
| 6,246,321 B1 | 6/2001 | Rechsteiner et al. |
| 6,282,496 B1 | 8/2001 | Chowdhary |
| 6,369,794 B1 | 4/2002 | Sakurai et al. |
| 6,428,490 B1 | 8/2002 | Kramer et al. |
| 6,493,652 B1 | 12/2002 | Ohlenbusch et al. |
| 6,496,695 B1 | 12/2002 | Kouji et al. |
| 6,513,381 B2 | 2/2003 | Fyfe et al. |
| 6,522,266 B1 | 2/2003 | Soehren et al. |
| 6,532,419 B1 | 3/2003 | Begin et al. |
| 6,539,336 B1 | 3/2003 | Vock et al. |
| 6,611,789 B1 | 8/2003 | Darley |
| 6,672,991 B2 | 1/2004 | O'Malley |
| 6,685,480 B2 | 2/2004 | Nishimoto et al. |
| 6,700,499 B2 | 3/2004 | Kubo et al. |
| 6,786,877 B2 | 9/2004 | Foxlin |
| 6,790,178 B1 | 9/2004 | Mault et al. |
| 6,813,582 B2 | 11/2004 | Levi et al. |
| 6,823,036 B1 | 11/2004 | Chen |
| 6,826,477 B2 | 11/2004 | Ladetto et al. |
| 6,836,744 B1 | 12/2004 | Asphahani et al. |
| 6,881,191 B2 | 4/2005 | Oakley et al. |
| 6,885,971 B2 | 4/2005 | Vock et al. |
| 6,898,550 B1 | 5/2005 | Blackadar et al. |
| 6,928,382 B2 | 8/2005 | Hong et al. |
| 6,941,239 B2 | 9/2005 | Unuma et al. |
| 6,959,259 B2 | 10/2005 | Vock et al. |
| 6,975,959 B2 | 12/2005 | Dietrich et al. |
| 7,010,332 B1 | 3/2006 | Irvin et al. |
| 7,020,487 B2 | 3/2006 | Kimata |
| 7,054,784 B2 | 5/2006 | Flentov et al. |
| 7,057,551 B1 | 6/2006 | Vogt |
| 7,072,789 B2 | 7/2006 | Vock et al. |
| 7,092,846 B2 | 8/2006 | Vock et al. |
| 7,148,797 B2 | 12/2006 | Albert |
| 7,155,507 B2 | 12/2006 | Hirano et al. |
| 7,158,912 B2 | 1/2007 | Vock et al. |
| 7,169,084 B2 | 1/2007 | Tsuji |
| 7,171,331 B2 | 1/2007 | Vock et al. |
| 7,173,604 B2 | 2/2007 | Marvit et al. |
| 7,177,684 B1 | 2/2007 | Kroll et al. |
| 7,200,517 B2 | 4/2007 | Darley et al. |
| 7,212,943 B2 | 5/2007 | Aoshima et al. |
| 7,220,220 B2 | 5/2007 | Stubbs et al. |
| 7,254,516 B2 | 8/2007 | Case et al. |
| 7,297,088 B2 | 11/2007 | Tsuji |
| 7,328,611 B2 | 2/2008 | Klees et al. |
| 7,334,472 B2 | 2/2008 | Seo et al. |
| 7,353,112 B2 | 4/2008 | Choi et al. |
| 7,387,611 B2 | 6/2008 | Inoue et al. |
| 7,397,357 B2 | 7/2008 | Krumm et al. |
| 7,428,471 B2 | 9/2008 | Darley et al. |
| 7,451,056 B2 | 11/2008 | Flentov et al. |
| 7,457,719 B1 | 11/2008 | Kahn et al. |
| 7,467,060 B2 | 12/2008 | Kulach et al. |
| 7,512,515 B2 | 3/2009 | Vock et al. |
| 7,526,402 B2 | 4/2009 | Tenanhaus et al. |
| 7,608,050 B2 | 10/2009 | Shugg |
| 7,617,071 B2 | 11/2009 | Darley et al. |
| 7,640,134 B2 | 12/2009 | Park et al. |
| 7,640,804 B2 | 1/2010 | Daumer et al. |
| 7,647,196 B2 | 1/2010 | Kahn et al. |
| 7,653,508 B1 | 1/2010 | Kahn et al. |
| 7,752,011 B2 | 7/2010 | Niva et al. |
| 7,753,861 B1 | 7/2010 | Kahn et al. |
| 7,774,156 B2 | 8/2010 | Niva et al. |
| 7,811,203 B2 | 10/2010 | Unuma et al. |
| 7,857,772 B2 | 12/2010 | Bouvier et al. |
| 7,881,902 B1 | 2/2011 | Kahn et al. |
| 7,889,085 B2 * | 2/2011 | Downey et al. ............ 340/573.1 |
| 7,892,080 B1 | 2/2011 | Dahl |
| 7,962,312 B2 | 6/2011 | Darley et al. |
| 7,987,070 B2 | 7/2011 | Kahn et al. |
| 2001/0027375 A1 | 10/2001 | Machida |
| 2002/0023654 A1 | 2/2002 | Webb |
| 2002/0027164 A1 | 3/2002 | Mault et al. |
| 2002/0089425 A1 | 7/2002 | Kubo et al. |
| 2002/0109600 A1 | 8/2002 | Mault et al. |
| 2002/0118121 A1 | 8/2002 | Lehrman et al. |
| 2002/0142887 A1 | 10/2002 | O'Malley |
| 2002/0151810 A1 | 10/2002 | Wong et al. |
| 2003/0018430 A1 | 1/2003 | Ladetto et al. |
| 2003/0048218 A1 | 3/2003 | Milnes et al. |
| 2003/0083596 A1 | 5/2003 | Kramer et al. |
| 2003/0093187 A1 | 5/2003 | Walker |
| 2003/0109258 A1 | 6/2003 | Mantyjarvi et al. |
| 2003/0139692 A1 | 7/2003 | Barrey et al. |
| 2003/0149526 A1 | 8/2003 | Zhou et al. |
| 2004/0172167 A1 | 9/2004 | Pasolini et al. |
| 2004/0204840 A1 | 10/2004 | Hashima |
| 2004/0219910 A1 | 11/2004 | Beckers |
| 2004/0225467 A1 | 11/2004 | Vock et al. |
| 2004/0236500 A1 | 11/2004 | Choi et al. |
| 2005/0033200 A1 | 2/2005 | Soehren et al. |
| 2005/0079873 A1 | 4/2005 | Caspi et al. |
| 2005/0107944 A1 | 5/2005 | Hovestadt et al. |
| 2005/0131736 A1 | 6/2005 | Nelson et al. |
| 2005/0202934 A1 | 9/2005 | Olrik et al. |
| 2005/0222801 A1 | 10/2005 | Wulff et al. |
| 2005/0232388 A1 | 10/2005 | Tsuji |
| 2005/0232404 A1 | 10/2005 | Gaskill |
| 2005/0234637 A1 | 10/2005 | Obradovich et al. |
| 2005/0238132 A1 | 10/2005 | Tsuji |
| 2005/0240375 A1 | 10/2005 | Sugai |
| 2005/0248718 A1 | 11/2005 | Howell et al. |
| 2006/0020177 A1 | 1/2006 | Seo et al. |
| 2006/0063980 A1 | 3/2006 | Hwang et al. |
| 2006/0064276 A1 | 3/2006 | Ren et al. |
| 2006/0080551 A1 | 4/2006 | Mantyjarvi et al. |
| 2006/0100546 A1 | 5/2006 | Silk |
| 2006/0136173 A1 | 6/2006 | Case et al. |
| 2006/0161377 A1 | 7/2006 | Rakkola et al. |
| 2006/0167387 A1 | 7/2006 | Buchholz et al. |
| 2006/0206258 A1 | 9/2006 | Brooks |
| 2006/0223547 A1 | 10/2006 | Chin et al. |
| 2006/0259268 A1 | 11/2006 | Vock et al. |
| 2006/0284979 A1 | 12/2006 | Clarkson |
| 2006/0288781 A1 | 12/2006 | Daumer et al. |
| 2007/0037605 A1 | 2/2007 | Logan et al. |
| 2007/0038364 A1 | 2/2007 | Lee et al. |
| 2007/0061105 A1 | 3/2007 | Darley et al. |
| 2007/0063850 A1 | 3/2007 | Devaul et al. |
| 2007/0067094 A1 | 3/2007 | Park et al. |
| 2007/0073482 A1 | 3/2007 | Churchill et al. |
| 2007/0082789 A1 | 4/2007 | Nissila et al. |
| 2007/0125852 A1 | 6/2007 | Rosenberg |
| 2007/0130582 A1 | 6/2007 | Chang et al. |
| 2007/0142715 A1 | 6/2007 | Banet et al. |
| 2007/0208531 A1 | 9/2007 | Darley et al. |
| 2007/0213126 A1 | 9/2007 | Deutsch et al. |
| 2007/0250261 A1 | 10/2007 | Soehren |
| 2007/0260418 A1 | 11/2007 | Ladetto et al. |
| 2007/0260482 A1 | 11/2007 | Nurmela et al. |
| 2008/0024364 A1 | 1/2008 | Frederick Taylor |
| 2008/0059061 A1 | 3/2008 | Lee |
| 2008/0140338 A1 | 6/2008 | No et al. |
| 2008/0165737 A1 | 7/2008 | Uppala |
| 2008/0167801 A1 | 7/2008 | Geelen |
| 2008/0171918 A1 | 7/2008 | Teller et al. |
| 2008/0231713 A1 | 9/2008 | Florea et al. |
| 2008/0254944 A1 | 10/2008 | Muri et al. |
| 2008/0311929 A1 | 12/2008 | Carro et al. |
| 2009/0043531 A1 | 2/2009 | Kahn et al. |
| 2009/0047645 A1 | 2/2009 | Dibenedetto et al. |

(56) References Cited

U.S. PATENT DOCUMENTS

| | | |
|---|---|---|
| 2009/0082994 A1 | 3/2009 | Schuler et al. |
| 2009/0138200 A1 | 5/2009 | Hunter |
| 2009/0213002 A1 | 8/2009 | Rani et al. |
| 2009/0216704 A1 | 8/2009 | Zheng et al. |
| 2009/0234614 A1 | 9/2009 | Kahn et al. |
| 2009/0319221 A1 | 12/2009 | Kahn et al. |
| 2010/0056872 A1 | 3/2010 | Kahn et al. |
| 2010/0057398 A1 | 3/2010 | Darley et al. |
| 2011/0066364 A1 | 3/2011 | Hale |

OTHER PUBLICATIONS

Ang, Wei Tech, et al, "Zero Phase Filtering for Active Compensation of Periodic Physiological Motion," Proc 1st IEEE / RAS-EMBS International Conference on Biomedical Robotics and Biomechatronics, Feb. 20-22, 2006, pp. 182-187.

Aylward, Ryan, et al, "Sensemble: A Wireless, Compact, Multi-User Sensor System for Interactive Dance," International Conference on New Interfaces for Musical Expression (NIME06), Jun. 4-8, 2006, pp. 134-139.

Baca, Arnold, et al, "Rapid Feedback Systems for Elite Sports Training," IEEE Pervasive Computing, Oct.-Dec. 2006, pp. 70-76.

Bakhru, Kesh, "A Seamless Tracking Solution for Indoor and Outdoor Position Location," IEEE 16th International Symposium on Personal, Indoor, and Mobile Radio Communications, 2005, pp. 2029-2033.

Bliley, Kara E, et al, "A Miniaturized Low Power Personal Motion Analysis Logger Utilizing MEMS Accelerometers and Low Power Microcontroller," IEEE EMBS Special Topic Conference on Microtechnologies in Medicine and Biology, May 12-15, 2005, pp. 92-93.

Bourzac, Katherine "Wearable Health Reports," Technology Review, Feb. 28, 2006, <http://www.techreview.com/printer_friendly_article_aspx?id+16431>, Mar. 22, 2007, 3 pages.

Cheng, et al, "Periodic Human Motion Description for Sports Video Databases," Proceedings of the Pattern Recognition, 2004, 5 pages.

Dao, Ricardo, "Inclination Sensing with Thermal Accelerometers", MEMSIC, May 2002, 3 pages.

Fang, Lei, et al, "Design of a Wireless Assisted Pedestrian Dead Reckoning System—The NavMote Experience," IEEE Transactions on Instrumentation and Measurement, vol. 54, No. 6, Dec. 2005, pp. 2342-2358.

Healey, Jennifer, et al, "Wearable Wellness Monitoring Using ECG and Accelerometer Data," IEEE Int. Symposium on Wearable Computers (ISWC'05), 2005, 2 pages.

Hemmes, Jeffrey, et al, "Lessons Learned Building TeamTrak: An Urban/Outdoor Mobile Testbed," 2007 IEEE Int. Conf. on Wireless Algorithms, Aug. 1-3, 2007, pp. 219-224.

Jones, L, et al, "Wireless Physiological Sensor System for Ambulatory Use," <http://ieeexplore.ieee.org/xpl/freeabs_all.jsp?tp=&arnumber=1612917&isnumber=33861>, Apr. 3-5, 2006.

Jovanov, Emil, et al, "A Wireless Body Area Network of Intelligent Motion Sensors for Computer Assisted Physical Rehabilitation," Journal of NeuroEngineering and Rehabilitation, Mar. 2005, 10 pages.

Kalpaxis, Alex, "Wireless Temporal-Spatial Human Mobility Analysis Using Real-Time Three Dimensional Acceleration Data," IEEE Intl. Multi-Conf. on Computing in Global IT (ICCGI'07), 2007, 7 pages.

Lee, Seon-Woo, et al., "Recognition of Walking Behaviors for Pedestrian Navigation," ATR Media Integration & Communications Research Laboratories, Kyoto, Japan, pp. 1152-1155.

Margaria, Rodolfo, "Biomechanics and Energetics of Muscular Exercise", Chapter 3, pp. 105-125, Oxford: Clarendon Press 1976.

Milenkovic, Milena, et al, "An Accelerometer-Based Physical Rehabilitation System," IEEE SouthEastern Symposium on System Theory, 2002, pp. 57-60.

Mizell, David, "Using Gravity to Estimate Accelerometer Orientation", Seventh IEEE International Symposium on Wearable Computers, 2003, 2 pages.

Ormoneit, D., et al (2000). Learning and tracking of cyclic human motion. Proceedings of NIPS 2000 (Neural Information Processing Systems), Denver, CO, pp. 894-900.

Otto, Chris, et al, "System Architecture of a Wireless Body Area Sensor Network for Ubiquitous Health Monitoring," Journal of Mobile Multimedia, vol. 1, No. 4, 2006, pp. 307-326.

Park, Chulsung, et al, "Eco: An Ultra-Compact Low-Power Wireless Sensor Node for Real-Time Motion Monitoring," IEEE Int. Symp. on Information Processing in Sensor Networks, 2005, pp. 398-403.

PCT/US2009/55558, International Search Report and Written Opinion, mailed Oct. 22, 2009, 11 pages.

PCT/US2011/024022, International Search Report and Written Opinion, mailed Mar. 15, 2011, 9 pages.

"Sensor Fusion," <www.u-dynamics.com>, accessed Aug. 29, 2008, 2 pages.

Shen, Chien-Lung, et al, "Wearable Band Using a Fabric-Based Sensor for Exercise ECG Monitoring," IEEE Int. Symp. on Wearable Computers, 2006, 2 pages.

Tapia, Emmanuel Munguia, et al, "Real-Time Recognition of Physical Activities and Their Intensities Using Wireless Accelerometers and a Heart Rate Monitor," IEEE Cont. on Wearable Computers, Oct. 2007, 4 pages.

Wang, Shu, et al, "Location Based Services for Mobiles: Technologies and Standards, LG Electronics MobileComm," IEEE ICC 2008, Beijing, pp. 1-66 (part 1 of 3).

Wang, Shu, et al, "Location Based Services for Mobiles: Technologies and Standards, LG Electronics MobileComm," IEEE ICC 2008, Beijing, pp. 67-92 (part 2 of 3).

Wang, Shu, et al, "Location Based Services for Mobiles: Technologies and Standards, LG Electronics MobileComm," IEEE ICC 2008, Beijing, pp. 93-123 (part 3 of 3).

Weckesser, P, et al, "Multiple Sensorprocessing for High-Precision Navigation and Environmental Modeling with a Mobile Robot," IEEE, 1995, pp. 453-458.

Weinberg, Harvey, "MEMS Motion Sensors Boost Handset Reliability" Jun. 2006, <http://www.mwrf.com/Articles/Print.cfm?ArticleID=12740>, Feb. 21, 2007, 3 pages.

Wixted, Andrew J, et al, "Measurement of Energy Expenditure in Elite Athletes Using MEMS-Based Triaxial Accelerometers," IEEE Sensors Journal, vol. 7, No. 4, Apr. 2007, pp. 481-488.

Wu, Winston H, et al, "Context-Aware Sensing of Physiological Signals," IEEE Int. Conf. on Engineering for Medicine and Biology, Aug. 23-26, 2007, pp. 5271-5275.

Yoo, Chang-Sun, et al, "Low Cost GPS/INS Sensor Fusion System for UAV Navigation," IEEE, 2003, 9 pages.

European Supplemental Search Report and Preliminary Examination. Jul. 17, 2014 (7 pages).

"Sensor Fusion," <http://www.u-dynamics.com/sensor_fusion/sensfuse-datasheet.pdf>, accessed Aug. 29, 2008, 2 pages.

\* cited by examiner

SENSOR FUSION FOR ACTIVITY IDENTIFICATION

This application is a continuation of U.S. patent application Ser. No. 14/061,701, filed on Oct. 23, 2013, now U.S. Pat. No. 8,784,309, issuing on Jul. 22, 2014, which is a continuation of U.S. patent application Ser. No. 13/476,962, filed on May 21, 2012, now U.S. Pat. No. 8,568,310, issued on Oct. 29, 2013, which is a divisional of U.S. patent application Ser. No. 12/202,206, filed on Aug. 29, 2008, now U.S. Pat. No. 8,187,182 issued on May 29, 2012.

FIELD OF THE INVENTION

This invention relates to using a plurality of sensors, and sensor fusion for more accurate calculation of user activity statistics.

BACKGROUND

The development of Micro-Electro-Mechanical Systems (MEMS) technology has enabled manufacturers to produce inertial sensors (e.g., accelerometers) that have a small size, cost, and power consumption. Global positioning system (GPS) sensors have also been developed that are of small size, cost and power consumption. Some manufacturers of unmanned aerial vehicles (UAVs) have begun using navigation systems that combine sensor readings of inertial sensors and sensor readings of GPS sensors via sensor fusion to improve navigation. UAVs always perform the same type of motions (flight in a forward direction). Therefore, the navigation systems are not required to identify different types of activities. Nor are the navigation systems capable of performing activity identification. Moreover, the navigation systems are also incapable of determining activity statistics associated with particular activities.

Recent advances have enabled inertial sensors and GPS sensors to be installed in a limited number of mobile commercial electronic devices such as cellular phones and portable computers. However, no such mobile devices are currently offered that perform sensor fusion to combine GPS sensor readings and inertial sensor readings.

BRIEF DESCRIPTION OF THE DRAWINGS

The present invention is illustrated by way of example, and not by way of limitation, and can be more fully understood with reference to the following detailed description when considered in connection with the following figures.

DETAILED DESCRIPTION

Embodiments of the present invention are designed to monitor human activity using multiple sensors. In one embodiment, a mobile device monitors accelerations using an inertial sensor. A user activity is identified based on the accelerations. Examples of user activities include walking, running, rollerblading, bicycling, etc. A first calculation is made of a user activity statistic associated with the user activity based on the accelerations. User activity statistics include periodic human motion counts, distance traveled, location, calories burned, etc. Location information is obtained by a location based sensor. A second calculation is made of the user activity statistic based on the location information. The final user activity statistic is calculated based on the first calculation and the second calculation.

Figure 1:
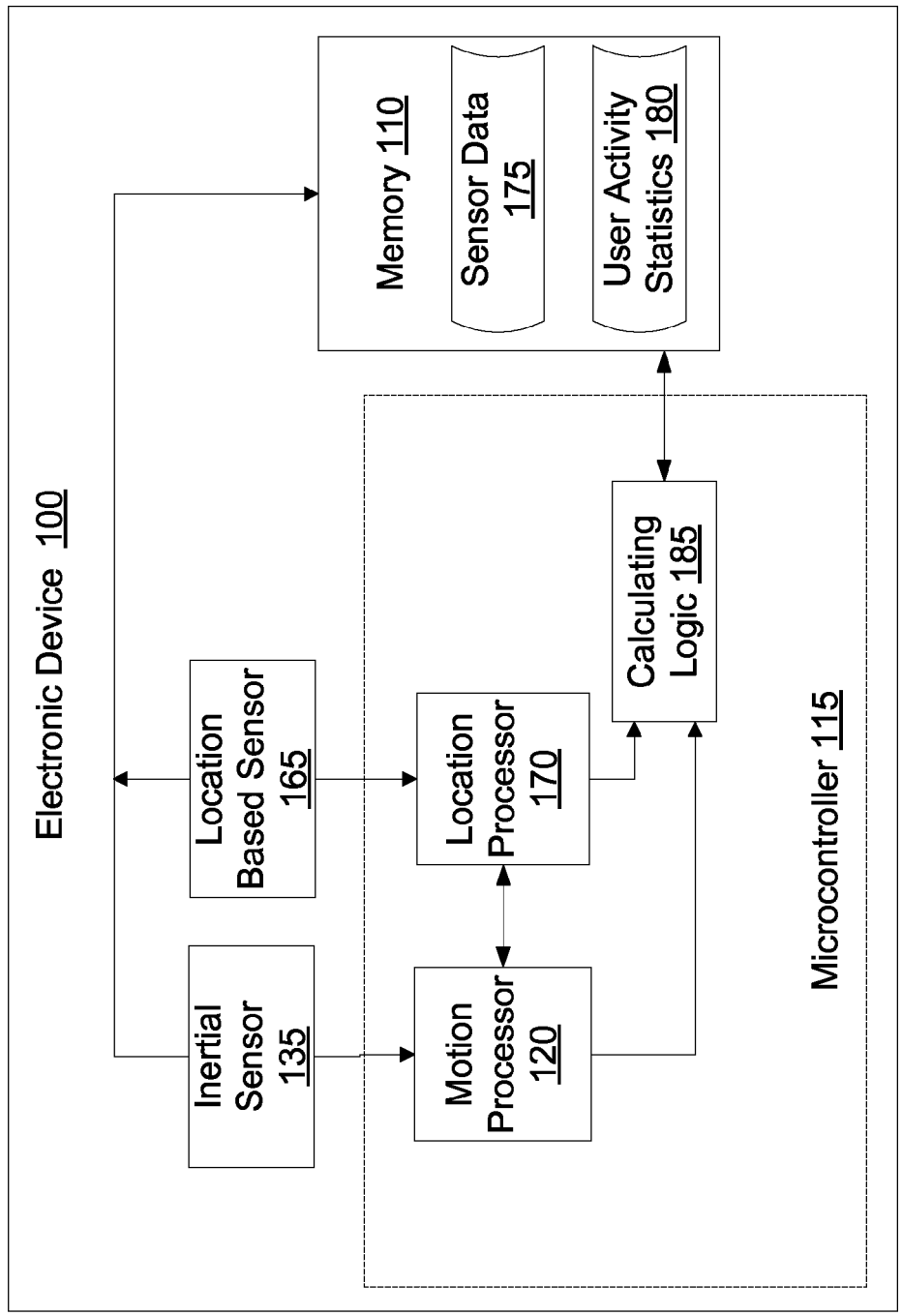
FIG. 1 is a block diagram illustrating an electronic device, in accordance with one embodiment of the present invention.

FIG. 1 is a block diagram illustrating an electronic device 100, in accordance with one embodiment of the present invention. Electronic device 100 may be a cellular phone, wrist watch, mp3 player, personal digital assistant (PDA), mobile game console, laptop computer, or any other device which can support at least two sensors and be carried by a user.

In one embodiment, the electronic device 100 is a portable electronic device that includes one or more inertial sensors 135 and one or more location based sensors 165. The inertial sensor 135 may measure accelerations along a single axis or multiple axes, and may measure linear as well as rotational (angular) accelerations. In one embodiment, one or more inertial sensors together provide three dimensional acceleration measurement data.

The inertial sensor 135 may generate acceleration measurement data 175 continuously, or at a sampling rate that may be fixed or variable. In one embodiment, the inertial sensor 135 receives a timing signal from a timer (not shown) to take measurements at the sampling rate.

The location based sensor 165 can include a single location based sensor, or multiple location based sensors (e.g., multiple different types of location based sensors). In one embodiment, the location based sensor 165 includes a global positioning system (GPS) sensor, which may include a GPS antenna and a GPS receiver. The GPS sensor obtains location information from one or more GPS satellites.

In one embodiment, the location based sensor 165 includes a network localization sensor. A network localization sensor determines a position by receiving signals from multiple sources that have known locations, and calculating the position based on the combined signals using trigonometric relations. Network localization sensors may determine location based on trilateration, multilateration and/or triangulation. The signals used to determine location may be radio frequency (RF) signals formatted according to the Bluetooth protocol, Zigbee protocol, wireless fidelity (WiFi) protocol, global system for mobile communications (GSM) protocol, 3G mobile communications protocol, etc. For example, a first network localization sensor may perform network triangulation using signals received from a mobile phone service provider's cell towers. In another example, a second network localization sensor may perform triangulation using wireless fidelity (WiFi) signals received from multiple nearby WiFi access points (e.g., hotspots).

In one embodiment, the location based sensor 165 includes a radio frequency identification (RFID) reader that reads transponders (e.g., passive integrated transponders (PITs)). Each transponder may report a specific location. When, for example, a transponder that reports location A is read, the location based sensor 165 knows to a high degree of certainty that the electronic device 100 is at location A. Alternatively, the location based sensor 165 may itself include a PIT that is read by an RFID reader at a known location. Upon the PIT being read by a particular RFID reader having a known location, the location based sensor 165 may learn its current location.

Multiple location based sensors 165 may be used separately or together. When used separately, each location based sensor 165 may independently determine a location of the electronic device 100, and report the location to a location processor 170. When used together, the capabilities of one location based sensor 165 can be used to augment the capabilities of another location based sensor 165. Examples of such cooperative use of location based sensors 165 include assisted GPS and enhanced GPS, in which location data reported by a network localization sensor is used to augment a GPS sensor. A single location may then be reported to the location processor 170.

The location based sensor 165 may generate location information continuously, or at a sampling rate that may be fixed or variable. In one embodiment, the location based sensor 165 receives a timing signal from a timer (not shown) to take measurements at the sampling rate. The location based sensor 165 may obtain location measurements at a sampling rate that is the same as or different from the sampling rate at which the inertial sensor 135 collects acceleration measurement data.

The location based sensor (or location based sensors) 165 can report a position of the electronic device 100 as a latitude and longitude, and may report a horizontal accuracy. In one embodiment, the horizontal accuracy of the location is reported as a confidence radius. For example, a location may be reported with a horizontal accuracy of 10 m, meaning that the reported location is accurate within a circle having a 10 m radius. Accuracy of the location may vary from about 10 m to about 300 m for location data obtained by a GPS sensor, depending on user location (e.g., in a city, under open sky, under a tree, in a building, etc.). The location information may further include an altitude, and may include a vertical accuracy. The location information may also include a time that the location was recorded.

In one embodiment, the inertial sensor 135 is coupled to a motion processor 120. The motion processor 120 processes acceleration measurement data received from the inertial sensor 135 to identify user activities. Examples of user activities that can be identified include walking, running, rollerblading, bicycling, cross country skiing, and other repetitive motion-based activities. The motion processor 120 also estimates user activity statistics based on the acceleration measurement data. User activity statistics may include multiple statistics associated with user activities (e.g., running and/or walking). Examples of user activity statistics include data about recent workouts, distance traveled per workout, distance traveled per day, average speed, highest speed, average incline of surface traveled, etc.

The motion processor 120 may identify a current user activity from a plurality of identifiable user activities. In one embodiment, the motion processor 120 identifies a user activity by monitoring for different events, each event indicative of a different type of activity. Events occur when certain motion criteria are satisfied (e.g., when a motion signature indicative of a step occurs within a certain period). In one embodiment, when enough events indicative of a particular user activity are detected, the motion processor 120 identifies the activity as being performed by the user. In one embodiment, events may include positive events (ones that must be met to classify a motion in a certain way) and negative events (ones that indicate that a motion cannot be classified certain way).

Once the motion processor 120 has identified a user activity, the motion processor 120 may apply a set of motion criteria specific to the identified activity to estimate one or more user activity statistics (e.g., to detect appropriate periodic human motions). Motion criteria may include acceleration thresholds (e.g., a step may be counted if the measured acceleration is below a first threshold and/or above a second threshold), acceleration comparison requirements (e.g., a step may be counted if a current measurement of acceleration is above or below one or more previous measurements of acceleration), cadence windows (e.g., a step may be counted if accelerations characteristic of a step occur within a certain timeframe as measured from a previous step), etc.

One type of user activity statistic that the motion processor 120 can determine is a number of steps (or other periodic human motions) taken. In one embodiment, a series of motion criteria are applied to the acceleration measurement data to detect steps or other periodic human motions. If each of the motion criteria are satisfied, a step may be identified, and counted. Alternatively, if a sufficient number of the motion criteria are satisfied, without a number of negative events, a step may be counted. In one embodiment, a different set of motion criteria may apply for running, for walking, and/or for other periodic human motions. For example, a first threshold and first cadence window may be used to determine if a step has occurred while a user is running, and a second threshold and second cadence window may be used to determine if a step has occurred while a user is walking.

Another type of user activity statistic that can be determined by the motion processor 120 is a distance traveled. A user's stride length can be determined for a step based on gait characteristics associated with the step. Examples of gait characteristics include step cadence, heel strike, and other gait characteristics that can be derived from acceleration measurements. For example, if a step cadence of 70 steps per minute and a specific heel strike are detected, a stride length of 2 ft. may be determined. Step detection and the calculated stride length of each step can then be used to calculate distance traveled.

In one embodiment, the stride length is determined by comparing gait characteristics to a stride length correlation model. The stride length correlation model correlates stride lengths to steps (or other periodic human motions) based on gait characteristics associated with the step (e.g., step cadence, heel strike, and other gait characteristics that can be derived from acceleration measurements). In one embodiment, the stride length correlation model includes a stride length algorithm that identifies a specific stride length when one or more gait characteristics are used as input. The stride length algorithm may vary depending on user attributes (e.g., depending on user weight, height, athletic ability, etc.).

In one embodiment, the stride length correlation model includes a stride length data structure (e.g., a lookup table, tree, etc.) that has a collection of entries. Each entry may associate a specific set of gait characteristics with a specific stride length. For example, the data structure may include a first entry associating a cadence of 70 steps per minute with a stride length of 2.6 feet, a second entry associating a cadence of 100 steps per minute with a stride length of 3 feet, etc. Each entry in the data structure may be associated with a range of gait characteristics. Therefore, for example, the cadences of 5-10 steps per minute may all be associated with a stride length of 2 feet in an entry. The use of a data structure may require less computing power than the use of the algorithm. The greater the number of entries, the more accurate the data structure, but the more memory it may require.

Other user activity statistics that the motion processor 120 can estimate include calories burned, route traveled, average speed of travel, maximum speed of travel, workout intensity, vertical distance traveled, and so on. These user activity statistics may be determined based on knowledge of user attributes (e.g., user weight, height, age, athletic ability, etc.), current user activity, and acceleration measurement data.

In one embodiment, steps (or other periodic human motions) may be accurately counted, and speed and distance traveled may be accurately determined by the motion processor 120, regardless of the placement and/or orientation of the electronic device 100 on a user. In a further embodiment, steps may be accurately counted, and speed and distance may be accurately determined, whether the electronic device 100 maintains a fixed orientation or changes orientation during use. In one embodiment, this can be achieved by monitoring the acceleration measurements to determine a dominant axis (axis that is most affected by gravity), and identifying a relationship between the axes of the inertial sensor and an orientation of the user based on the dominant axis.

In one embodiment, the motion processor 120 determines an accuracy of the calculated user activity statistics, as well as a confidence for the determined user activity. The accuracy can be determined based on the regularity (e.g., repeatability) of the user's motions, a number of positive events and negative events that are identified, motion criteria that are satisfied, etc. In one embodiment, the accuracy/confidence of the user activity and the user activity statistics are reported as a percentage of certainty. For example, the motion processor 120 may determine that there is a 94% likelihood that the user is walking at a cadence of 25 steps per minute. Alternatively, the confidence may be reported as a standard deviation, probability distribution, etc. In one embodiment, the motion processor 120 can report multiple user activities, and a likelihood that each is being performed. For example, the motion processor 120 may determine that there is a 35% likelihood that the user is running and a 65% likelihood that the user is speed walking.

In one embodiment, the map is used to plan a path between a starting location and an ending location. Path planning is described in greater detail below with reference to FIG. 7. In one embodiment, the map is used to direct a user through a path and/or to provide instructions to the user as the user traverses the path. Such an embodiment is described in greater detail below with reference to FIG. 8.

Referring to FIG. 1, in one embodiment, the location based sensor 165 is coupled to a location processor 170. The location processor 170 processes location measurement data received from the location based sensor 165. Based on the location information, the location processor 170 estimates user activity statistics such as speed of travel, route traveled, etc.

In one embodiment, the location processor 165 receives location information from multiple location based sensors 165. The location processor 170 may determine which of the location based sensor 165 is providing the most accurate location information, and use that location information to estimate user activity statistics. In one embodiment, the location processor 170 determines an accuracy of each of the user activity statistics that it estimates. The accuracy of the user activity statistics may be determined based on an accuracy of the location information reported by the location based sensor 165.

In one embodiment, the location processor 170 includes a map (or has access to a map, such as from a web mapping service). The user location may be compared to the map to determine the type of terrain that the user is traveling on. For example, the location processor 170 may determine that the user is traveling on a paved sidewalk, on a dirt trail, on a track, in a building, etc.

In one embodiment, the location processor 170 automatically performs an action when a predetermined location is identified. The action may be initiating a run application, or another appropriate action. The predetermined locations may be configured by a user. Additionally, some predetermined locations may be set by default. For example, gym locations may be configured by default so that a sports training application is automatically launched if a user location matches a location of a gym. In one embodiment, locations of particular items of training equipment within a gym can also be set. These locations may be identified, for example, using an RFID reader. The electronic device 100 can then determine information about the training equipment on which a user is training to more accurately log a workout. Alternatively, the user may indicate such locations. Alternatively a map of the gym layout may be acquired, which specifies such locations.

In one embodiment, the location processor 170 can set the predetermined location and/or the action based on repeated user behavior. For example, if the user typically starts a run at a first location and stops the run at a second location, these locations may be automatically recorded into memory, and associated with a run application. Of course, as at a track, the first and the second location may be the same location. The run application may then automatically be started when the user is located at the first location, and may automatically be terminated when the user is located at the second location. Therefore, the user may perform a run, and have the run recorded, without having to manually launch a run application.

In one embodiment, the motion processor 120 is connected with the location processor 170. The location processor 170 may send location information and/or estimated user activity statistics (including estimated accuracies) to the motion processor 120. The motion processor 120 may compare the received data to the user activity and/or the user activity statistics estimated by the motion processor 120. If the received data has a high accuracy and the user activity and/or estimated user activity statistic calculated by the motion processor 120 have a low accuracy, the motion processor 120 may determine a new user activity and/or estimate a new user activity statistic. For example, if the motion processor 120 had originally determined that the user activity is walking, and the location processor 170 reports with a high degree of accuracy that the user is traveling at a speed that exceeds a user's maximum walking speed, the motion processor 120 may determine that the user is running, or that the user is riding in a car.

In one embodiment, if the location information (GPS-based, network triangulation, etc.) has a high accuracy, and the user activity and/or user activity statistics calculated by the motion processor have a low accuracy, the motion processor uses the location information to perform calibration. In one embodiment, the motion processor 120 calibrates a stride length correlation model using the location information.

In one embodiment, motion processor 120 calibrates a stride length correlation model based on received location information that identifies a distance traveled. Such received location information may be correlated to gait characteristics that were collected while the received distance was walked or run. This correlation may then be compared to the stride length correlation model. If the correlation based on the received location information does not match the stride length correlation model, then the stride length correlation model may be modified or replaced.

In one embodiment, calibrating the stride length correlation model includes generating a new data structure using a data structure generation algorithm. The data structure generation algorithm may use as inputs user attributes (e.g., height, weight, age, etc.) and/or a stride length vs. gait characteristic correlation determined based on received distance information. Therefore, a new data structure can be produced that is tailored to user attributes of a specific user and/or based on empirical data taken of the specific user. Each entry in the new data structure may be more accurate for the user than entries in an uncalibrated data structure.

In another embodiment, calibrating the stride length correlation model includes adjusting entries in an existing data structure. Such adjustments may include shifting entries (e.g., adjusting entry values up or down), compressing entries (e.g., causing entries to represent a smaller range of gait characteristics), stretching entries (e.g., causing entries to represent a greater range of gait characteristics), scaling entries (e.g., multiplying entries by a percentage or scaling factor), etc. Adjustments may be made based on one or more of user attributes and a stride length vs. gait characteristic correlation determined based on received distance information. For example, a global shift may be applied to entries if a user walked 1 mile, but a distance of 1.5 miles was measured. Such a global shift could include shifting down the entries to reflect that the actual stride length is shorter than represented by the data structure. Alternatively, if only a few entries in the data structure are off, then only those entries may be shifted.

In yet another embodiment, calibrating the stride length correlation model includes modifying a stride length algorithm. Constants and/or variables that apply to user attributes may be modified. Moreover, adjustments may be made to the algorithm based on a stride length vs. gait characteristic correlation determined based on received distance information.

Calibration logic 220 may further calibrate an incline adjustment factor (not shown). The incline adjustment factor may be applied to the stride length correlation data when an incline is detected. For example, when a user walks uphill, the user is likely to take smaller steps than when that user walks on level terrain. This difference in stride length may be accounted for using the incline adjustment factor. A value of the incline adjustment factor that is applied to the stride length correlation model may depend on a degree of incline and on user attributes. The incline adjustment factor may be calibrated in the manners discussed above with reference to the stride length correlation model.

The motion processor 120 may also send estimated user activity statistics to the location processor 170. The location processor 170 may compare the received user activity statistics to user activity statistics estimated by the location processor 170 and/or to location information received from the location based sensor 165. If the received user activity statistics have a high accuracy, the location processor 170 may use the received user activity statistics to determine that the location based sensor 165 has not locked in on a GPS signal yet, or to lower the accuracy rating of the location information from the location based sensor 165.

In one embodiment, the motion processor 120 and location processor 170 are connected with a calculating logic 185. The estimated user activity statistics determined by each of the location processor 170 and the motion processor 120 are reported to the calculating logic 185, along with confidence interval of the estimations. The calculating logic 185 combines the two estimated user activity statistics to calculate more accurate final user activity statistics. The calculating logic 185 can use information from the motion processor 120 and the location processor 170 in conjunction to accurately count steps, determine speed of travel, determine distance traveled, etc.

In one embodiment, the calculating logic 185 applies a weight to each of the received user activity statistic estimations based on the reported accuracy of the estimations. The reported accuracy may range from around 1% accuracy to around 99% accuracy. In example, if the location processor 170 generated an estimation for a distance traveled that was 10 miles, with an 80% accuracy, and the motion processor 120 generated a distance traveled estimation of 11 miles with a 90% accuracy, these estimations may be combined as follows: $8/17(10)+9/17(11)=10.26$ miles. Alternatively, other algorithms may be used to combine the user activity statistics. For example, some user activity statistic estimations of the motion processor 120 may be weighted more heavily than those with an equivalent accuracy rating from the location processor 170. In one embodiment, if an accuracy rating of a user activity statistic estimated by a processor falls below a threshold, the estimation associated with the accuracy rating is not used at all. In such an instance, the calculating logic 185 may completely rely upon the estimation of the other processor(s).

In one embodiment, the location based sensor 165, inertial sensor 135 and calculating logic 185 are connected with a memory 110. Memory 110 may include one or more of volatile memory (e.g., random access memory (RAM)), nonvolatile memory (e.g., read only memory (ROM), or flash memory), a hard disk drive, an optical drive, etc. Memory 110 may comprise multiple memories, i.e. a RAM memory used as a buffer, and a flash memory used to store other data. The location based sensor 165 and inertial sensor 135 store sensor data 175 (e.g., acceleration measurement data and location information) in memory 110. In one embodiment, a buffer may collect acceleration measurement data and/or location information, and the buffered data may be used by motion processor 120 and/or location processor 170 for their calculations. In such an embodiment, motion processor 120 and/or location processor 170 may also be connected to memory 110. In one embodiment, once the calculating logic 185 calculates user activity statistics 180, it stores them in memory 110.

In one embodiment, motion processor 120, location processor 170 and calculating logic 185 are logics executed by a microcontroller 115, field programmable gate array (FPGA), application specific integrated circuit (ASIC), or other dedicated processing unit. In another embodiment, one or more of the motion processor 120, location processor 170 or calculating logic 185 may be logics executed by a central processing unit. Alternatively, one or more of the motion processor 120, location processor 170 or calculating logic 185 may include a state machine (e.g., an internal logic that knows how to perform a sequence of operations), a logic circuit (e.g., a logic that goes through a sequence of events in time, or a logic whose output changes immediately upon a changed input), or a combination of a state machine and a logic circuit.

Figure 2:
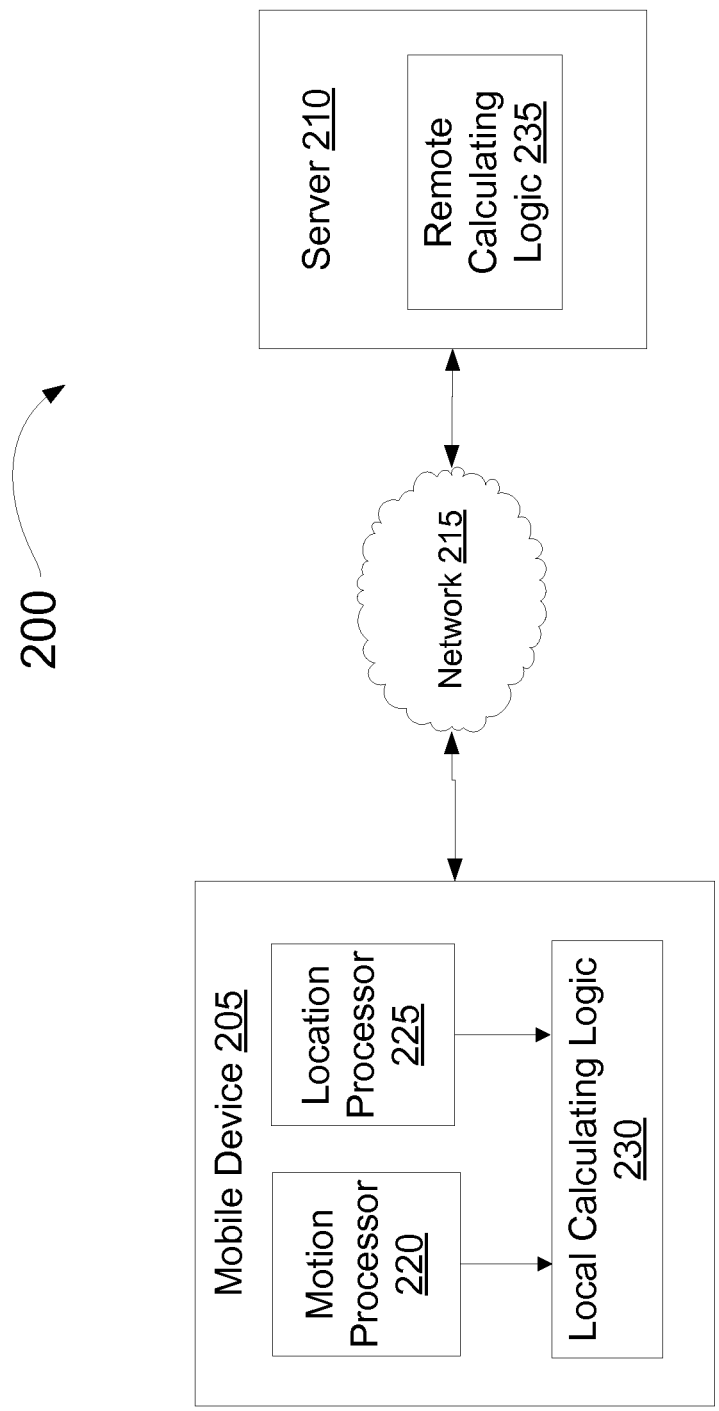
FIG. 2 illustrates a block diagram of an activity monitoring system, in accordance with one embodiment of the present invention.

FIG. 2 illustrates a block diagram of an activity monitoring system 200, in accordance with one embodiment of the present invention. The activity monitoring system 200 may monitor the activity of one or more users connected thereto. Records of such user activity may be maintained by the activity monitoring system 200. In one embodiment, the activity monitoring system 200 includes a mobile device 205 and a server 210.

In one embodiment, the mobile device 205 operates in conjunction with the server 210 to determine step count, speed of travel, distance traveled, and/or other user activity statistics. In the illustrated embodiment, mobile device 205 and server 210 are connected via a network 210, which may be a public network (e.g., internet) or private network (e.g., local area network (LAN), intranet, etc.). Alternatively, connections may be established directly between server 210 and mobile device 205. Wireless connections may be established (directly between devices or via network 215) using any wireless data transfer protocol, such as Bluetooth, radiofrequency (RF), wireless local area network (WLAN), infrared, cellular networks including global system for mobile communications (GSM), code division multiple access (CDMA), integrated digital enhanced network (iDEN), etc. Wired connections may be established using firewire, Ethernet, universal serial bus (USB), etc.

Mobile device 205 may be a mobile phone, PDA, pedometer, etc. In one embodiment, the mobile device 105 corresponds to electronic device 100 of FIG. 1. In a further embodiment, the mobile device 205 includes a motion processor 220 and a location processor 225. The motion processor 220 and location processor 225 in one embodiment operate as described in FIG. 1 with reference to location processor 170 and motion processor 120.

Motion processor 220 and location processor 225 are connected to a local calculating logic 230. The local calculating logic 230 receives user activity statistic estimations from the motion processor 220 and location processor 225, and calculates user activity statistics from the estimations on the fly (in real time). In the context of a sports application, this enables a user to be constantly apprised of his or her workout progress. However, in mobile devices 205 that have limited processing power, and/or that can dedicate only minimal processing power to the motion processor 220, location processor 225 and local calculating logic 230, the calculated user activity statistics may have reduced accuracy. To improve the accuracy of calculated user activity statistics, user activity statistics may be calculated by server 210 in one embodiment.

Server 210 may be a personal computer (desktop or laptop), network server, game kiosk, etc. Server 210 may receive user activity statistics, acceleration measurement data, user characteristics, etc. from the mobile device 205 directly or via the network 215. In one embodiment, server 210 includes a remote calculating logic 235. Remote calculating logic 235 uses the received user activity statistics, acceleration measurement data, user characteristics, etc. to recalculate the user activity statistics. The server 210 may have more processing power than mobile device 205, and may calculate the user activity statistics to a higher level of accuracy. In one embodiment, remote calculating logic 235 calculates user activity statistics, and transmits the calculated user activity statistics to the mobile device pseudo-real time. Such transmissions and calculations may be made pseudo-real time where a connection of sufficient bandwidth (a connection in which constant acceleration data, location data and user activity statistics can be transmitted with minimal lag) is established between the mobile device 205 and the server 210. In another embodiment, the remote calculating logic 235 recalculates the user activity statistics after a user activity has ended (e.g., after the user has finished a run). The server 210 can reconstruct an entire user event/activity after the fact with increased accuracy.

Figure 3:
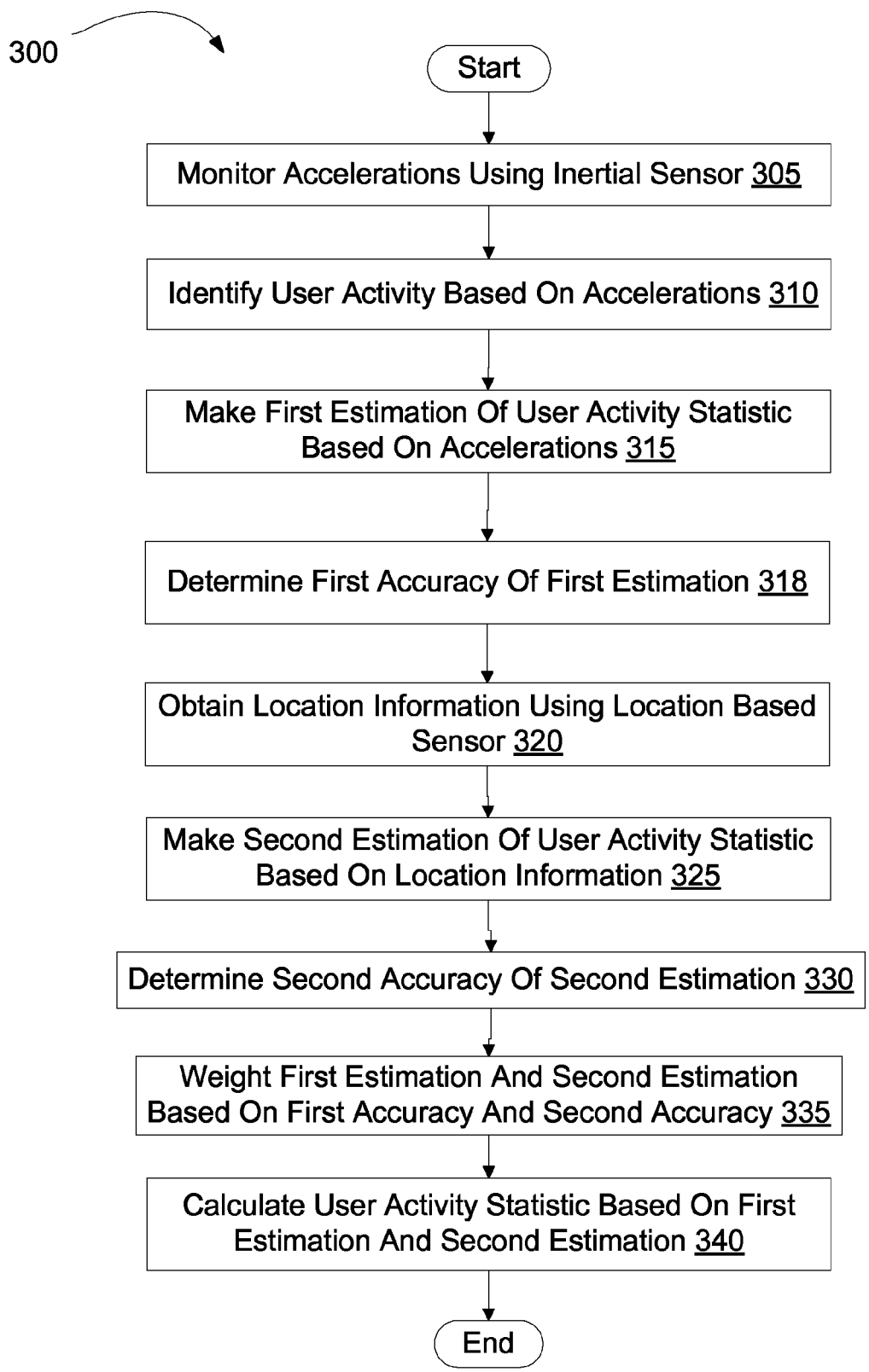
FIG. 3 illustrates a flow diagram for a method of monitoring human activity using an inertial sensor and a location based sensor, in accordance with one embodiment of the present invention.

FIG. 3 illustrates a flow diagram for a method 300 of monitoring human activity using an inertial sensor and a location based sensor, in accordance with one embodiment of the present invention. The method may be performed by processing logic that may comprise hardware (e.g., circuitry, dedicated logic, programmable logic, microcode, etc.), software (such as instructions run on a processing device), or a combination thereof. In one embodiment, method 300 is performed by the electronic device 100 of FIG. 1.

Referring to FIG. 3, method 300 includes monitoring accelerations (block 305). Monitoring accelerations may include obtaining acceleration measurement data from one or more inertial sensors and/or other acceleration monitoring devices. At block 310, a motion processor processes the accelerations to identify a user activity. Examples of user activities that can be identified include walking, running, bicycling, rollerblading, etc. In one embodiment, the user activity is identified by monitoring for different events, each event indicative of a different type of activity. When enough events indicative of a particular user activity are detected, the user activity may be identified.

At block 315, the motion processor makes a first estimation of a user activity. The user activity statistic may be estimated based on the acceleration measurement data. User activity statistics may include multiple statistics associated with user activities (e.g., running and/or walking). Examples of user activity statistics include data about recent workouts, distance traveled per workout, distance traveled per day, average speed, highest speed, average incline of surface traveled, etc. User activity statistics may be identified by applying a set of motion criteria specific to the identified activity. Motion criteria may include acceleration thresholds (e.g., a step may be counted if the measured acceleration is below a first threshold and/or above a second threshold), acceleration comparison requirements (e.g., a step may be counted if a current measurement of acceleration is above or below one or more previous measurements of acceleration), cadence windows (e.g., a step may be counted if accelerations characteristic of a step occur within a certain timeframe as measured from a previous step), etc.

At block 318, a first accuracy of the first estimation is determined. The first accuracy may be in the form of a percentage of accuracy, a standard deviation, or other confidence rating.

At block 320, a location processor obtains location information using a location based sensor. Examples of location based sensors include a GPS sensor, a network localization sensor, a transponder, etc. At block 325, the location processor makes a second estimation of the user activity statistic based on the location information. At block 330, the location processor determines accuracy for the second estimation.

At block 335, a calculating logic weights the first estimation and the second estimation based on the first accuracy and the second accuracy. The calculating logic may be a local calculating logic (e.g., that operates on a mobile device on which the location processor and motion processor operate) or a remote calculating logic (e.g., that is hosted by a server). At block 340, the calculating logic calculates the user activity statistic based on the first estimation and the second estimation. The user activity statistic may be calculated on the fly, or after a user activity has ended. If this process was calculated at the end of the workout, the method then ends. If the process was calculated while the workout was still going on, the process returns to block 315 to continue monitoring.

Figure 4:
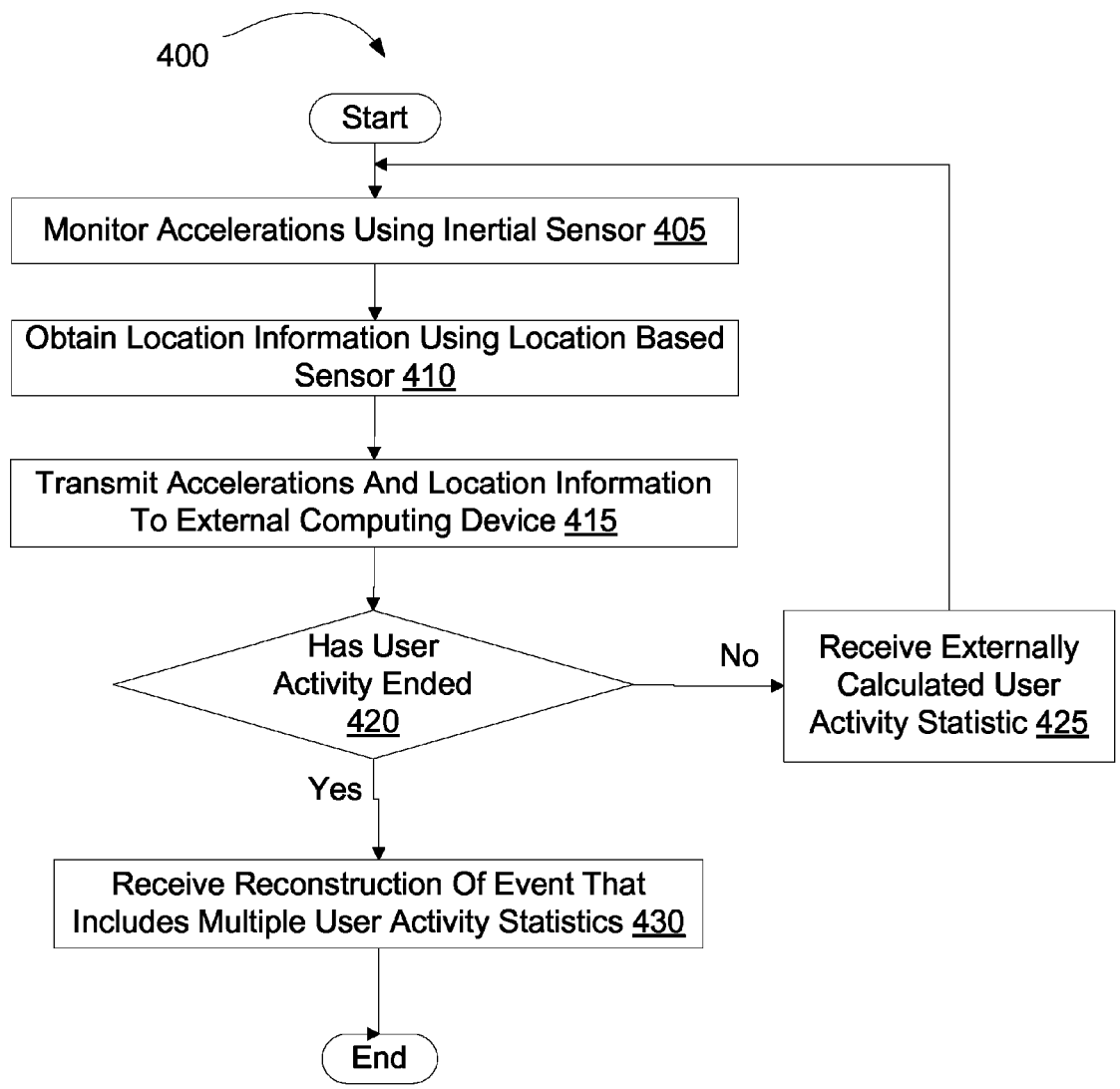
FIG. 4 illustrates a flow diagram for a method of monitoring human activity using an inertial sensor and a location based sensor, in accordance with another embodiment of the present invention.

FIG. 4 illustrates a flow diagram for a method 400 of monitoring human activity using an inertial sensor and a location based sensor, in accordance with another embodiment of the present invention. The method may be performed by processing logic that may comprise hardware (e.g., circuitry, dedicated logic, programmable logic, microcode, etc.), software (such as instructions run on a processing device), or a combination thereof. In one embodiment, method 400 is performed by the monitoring system 200 of FIG. 2.

Referring to FIG. 4, method 400 includes monitoring accelerations by a mobile device (block 405). Monitoring accelerations may include obtaining acceleration measurement data from one or more inertial sensors and/or other acceleration monitoring devices. At block 410, the mobile device obtains location information using a location based sensor. At block 415, the accelerations and the location information are transmitted to an external computing device (e.g., a server). In one embodiment, the location information and accelerations are transmitted wirelessly (e.g., via WiFi, GSM, 3G, Bluetooth, etc.).

At block 420, it is determined whether a user activity has ended. Such a determination may be made by the mobile device or by the external device. If the user activity has ended, the method proceeds to block 430. If the user activity has not ended, the method proceeds to block 425.

At block 425, the mobile device receives a user activity statistic that has been calculated by the external computing device. In one embodiment, this user activity statistic may be displayed to the user. The method then returns to block 405 to continue monitoring for accelerations.

At block 430, the mobile device receives a calculated final activity data, or reconstruction, of an event that includes multiple user activity statistics. The event may be a workout session (e.g., a run), and may include, for example, number of laps, distance traveled, route traveled, number of steps, average running speed, and so on. The final activity data may alter the activity data that was displayed to the user during the work-out. However, the final activity data will be more accurate, in one embodiment, since it will include data from multiple sensors.

Figure 5A:
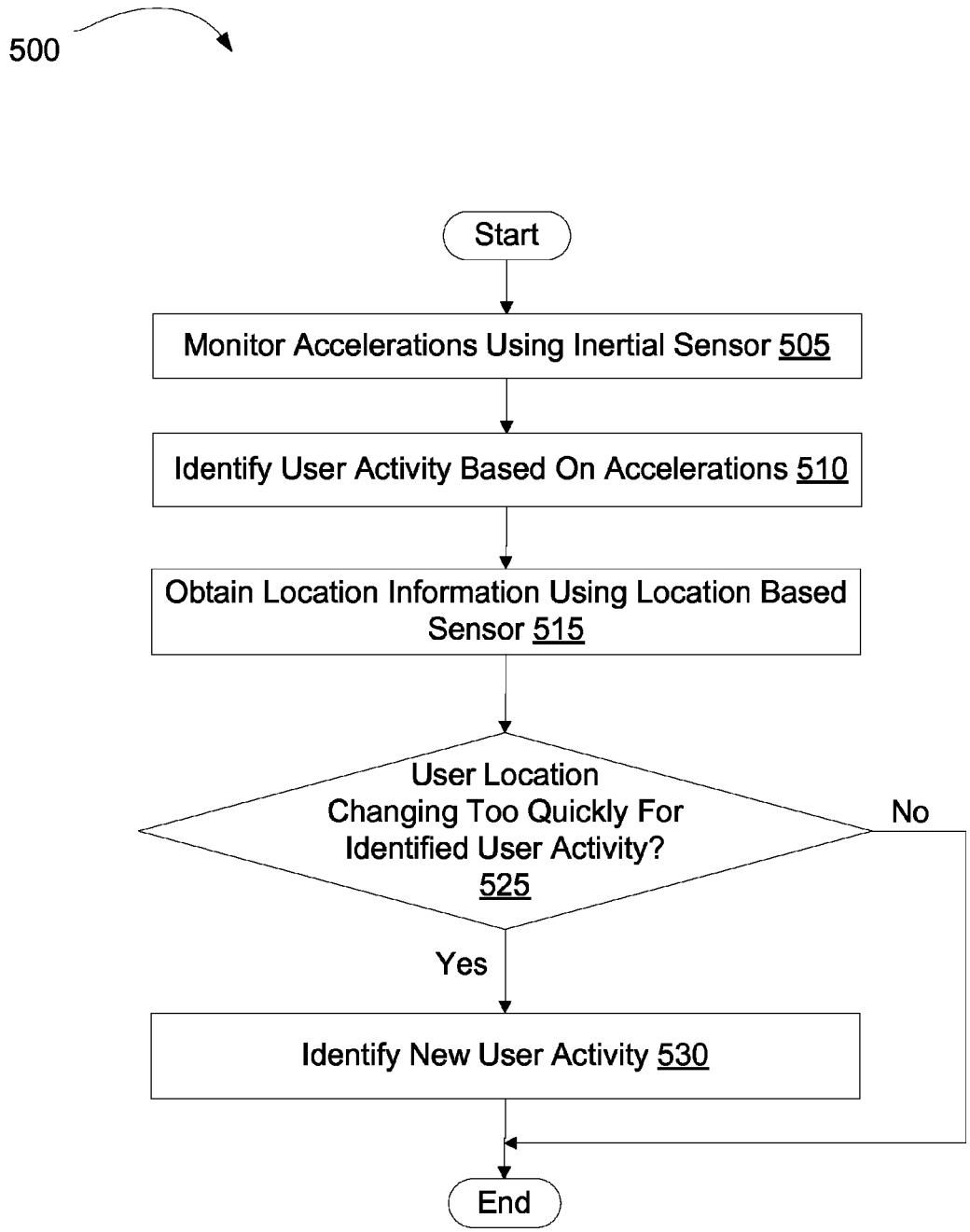
FIG. 5A illustrates a flow diagram for a method of filtering user activities based on location information, in accordance with one embodiment of the present invention.

FIG. 5A illustrates a flow diagram for a method 500 of filtering user activities based on location information, in accordance with one embodiment of the present invention. The method may be performed by processing logic that may comprise hardware (e.g., circuitry, dedicated logic, programmable logic, microcode, etc.), software (such as instructions run on a processing device), or a combination thereof. In one embodiment, method 500 is performed by the electronic device 100 of FIG. 1.

Referring to FIG. 5A, method 500 includes monitoring accelerations using an inertial sensor housed in a mobile device (block 505). At block 510, a motion processor processes the accelerations to identify a user activity. At block 515, a location processor obtains location information using a location based sensor. In one embodiment, the location information is a latitude and longitude. In one embodiment, a location processor utilizes map data to map the latitude and longitude to a map location.

At block 525, the accuracy of the user activity is verified using the location information. The mobile device can determine, for example, whether a user location has changed too quickly for the identified user activity. For example, if the user is moving at a speed of around 50 mph, it can be determined that the user is not walking. For another example, if the user is jogging at a steady pace, but the location data indicates that the user is travelling through various buildings, there is a mismatch between the user activity and the map location information. If the location information excludes the identified user activity, the method proceeds to block 530, and a new user activity is identified. In another embodiment, the accuracy rating of the user activity and/or location information is changed due to the mismatch.

If the location information does not exclude the calculated user activity, the method ends.

Figure 5B:
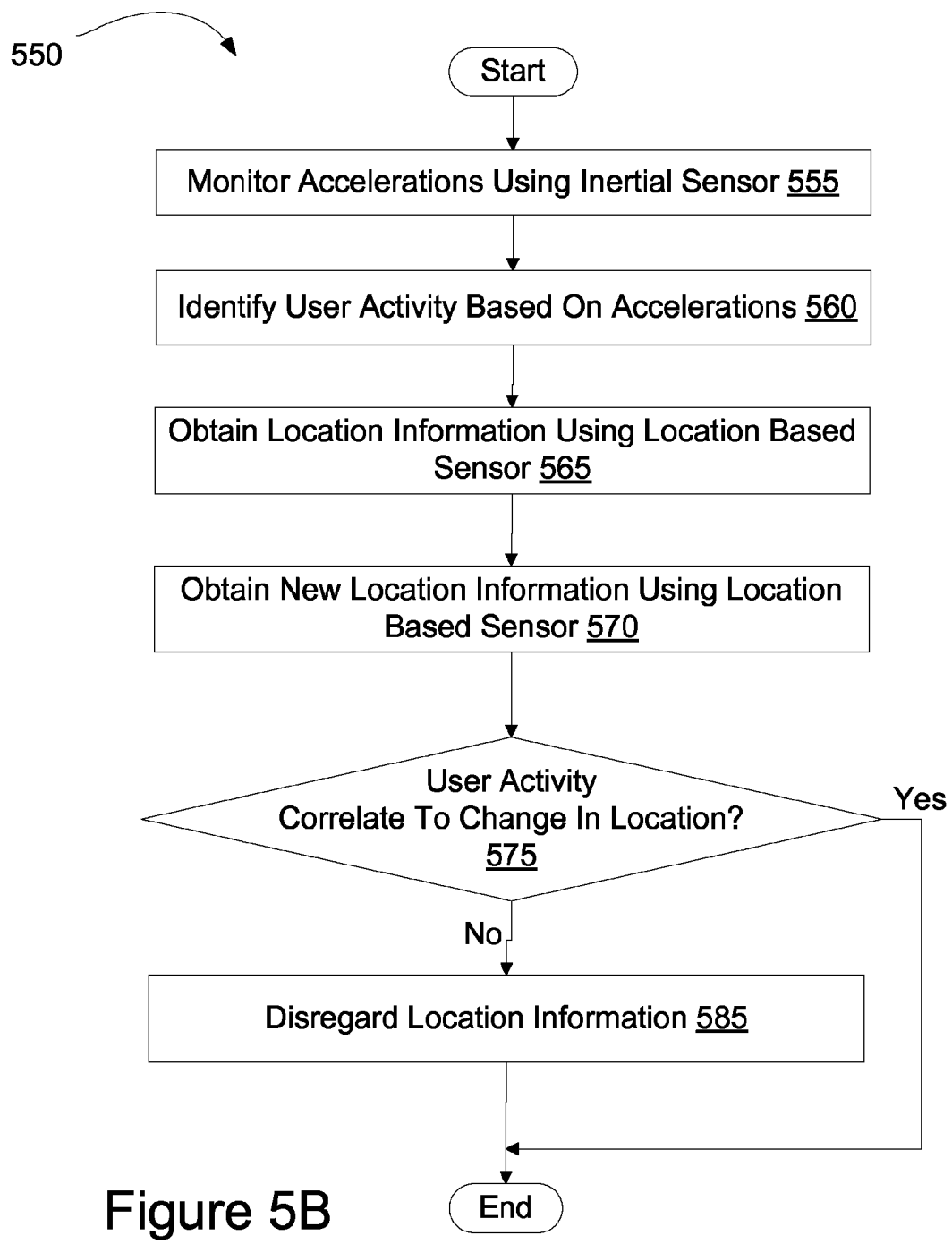
FIG. 5B illustrates a flow diagram for a method of filtering location information based on acceleration measurements, in accordance with one embodiment of the present invention.

FIG. 5B illustrates a flow diagram for a method 550 of filtering location information based on acceleration measurements, in accordance with one embodiment of the present invention. The method may be performed by processing logic that may comprise hardware (e.g., circuitry, dedicated logic, programmable logic, microcode, etc.), software (such as instructions run on a processing device), or a combination thereof. In one embodiment, method 550 is performed by the electronic device 100 of FIG. 1.

Referring to FIG. 5B, method 550 includes monitoring accelerations using an inertial sensor housed in a mobile device (block 555). At block 560, a motion processor processes the accelerations to identify a user activity.

At block 565, a location processor obtains location information using a location based sensor. At block 570, the location processor obtains new location information using the location based sensor. At block 575, the location processor compares the change in location to the user activity and/or the accelerations. If the user activity correlates to the change in location, the method ends. If the user activity does not correlate to the change in location, the method proceeds to block 585, and the location information is disregarded. The method then ends.

Figure 6:
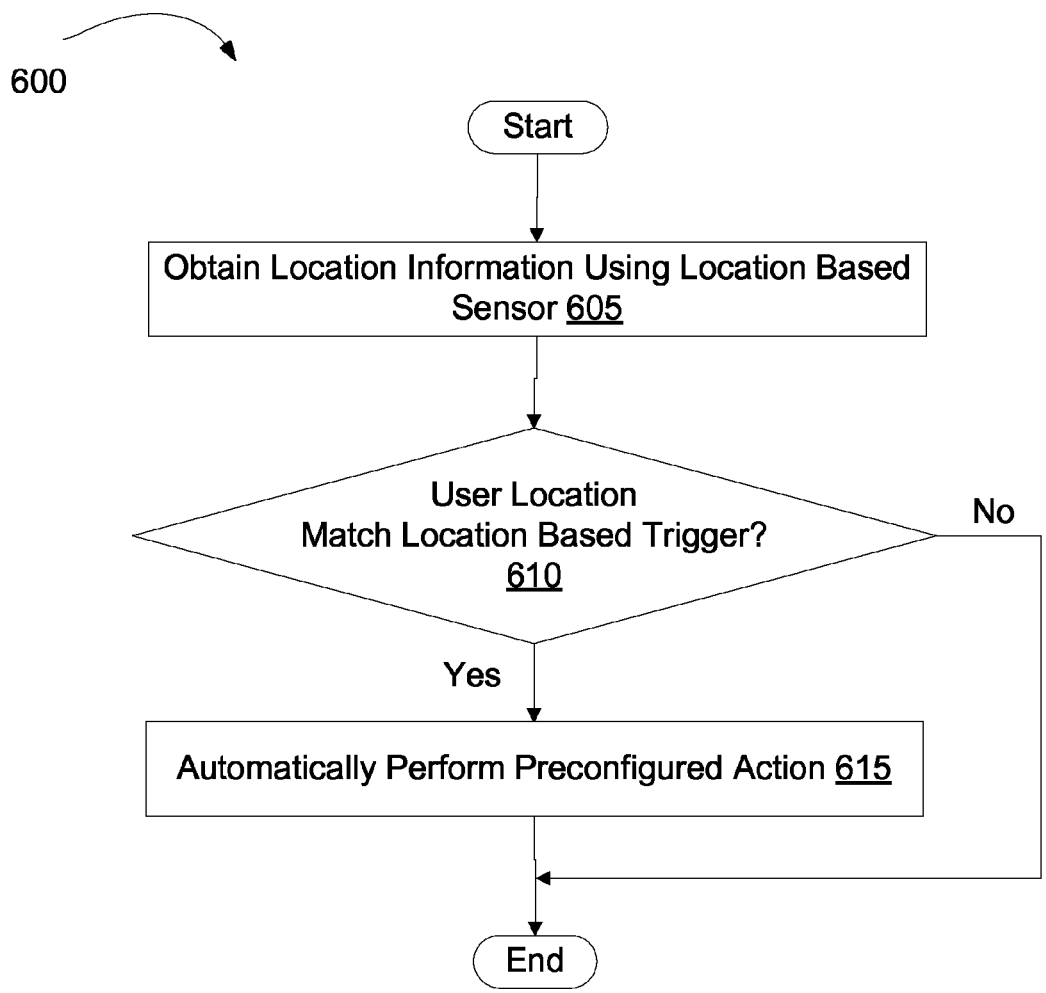
FIG. 6 illustrates a flow diagram for a method of automatically initiating actions based on location measurements, in accordance with one embodiment of the present invention.

FIG. 6 illustrates a flow diagram for a method 600 of automatically initiating actions based on location measurements, in accordance with one embodiment of the present invention. The method may be performed by processing logic that may comprise hardware (e.g., circuitry, dedicated logic, programmable logic, microcode, etc.), software (such as instructions run on a processing device), or a combination thereof. In one embodiment, method 600 is performed by the electronic device 100 of FIG. 1.

Referring to FIG. 6, method 600 includes obtaining location information using a location based sensor (block 605). At block 610, a location processor determines whether a current location matches a location based trigger. The location based trigger may have been programmed by a user, or may have been automatically determined based on repeated user behavior. For example, if a user is detected to repeatedly begin a run at a particular location, a run application may be automatically initiated when the user is detected to be at the particular location. If the current location matches a location based trigger, the method proceeds to block 615. Otherwise, the method ends.

At block 615, a preconfigured action is automatically performed (e.g., starting a run application). The method then ends.

Figure 7:
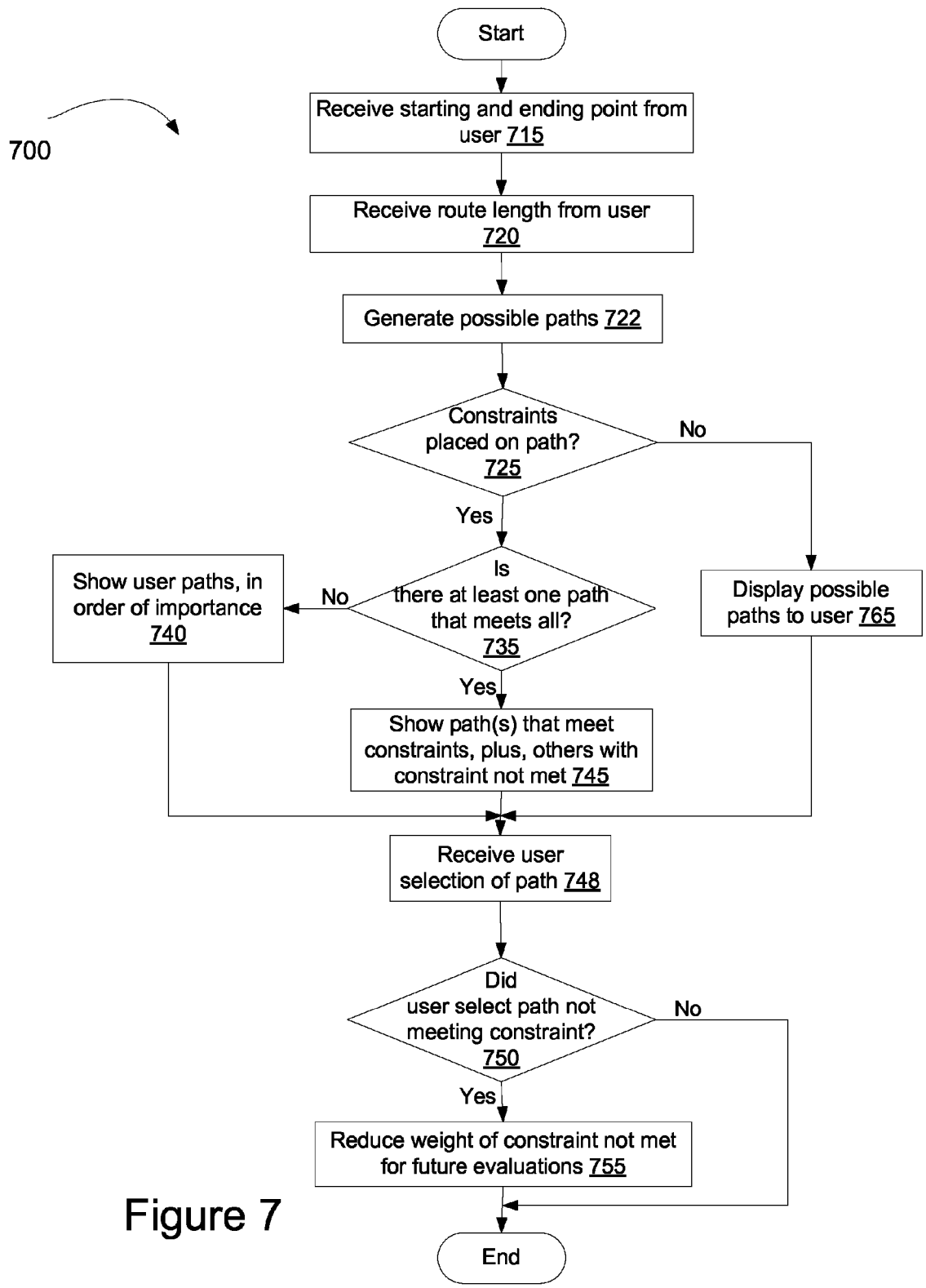
FIG. 7 illustrates a flow diagram for a method of planning a route, in accordance with one embodiment of the present invention.

FIG. 7 illustrates a flow diagram for a method 700 of planning a route, in accordance with one embodiment of the present invention. The method may be performed by processing logic that may comprise hardware (e.g., circuitry, dedicated logic, programmable logic, microcode, etc.), software (such as instructions run on a processing device), or a combination thereof. In one embodiment, method 700 is performed by the electronic device 100 of FIG. 1.

Referring to FIG. 7, at block 715, an electronic device receives a starting point and an end point from a user. At block 720, the electronic device receives a route length from the user. At block 722, the method generates one or more possible paths between the starting point and the end point.

At block 725, the method determines whether any constraints have been placed on paths between the starting point and the ending point. Examples of constraints include number of turns, amount of vertical distance traveled, preferred types of terrain to travel over, estimated time to completion, and so on. Constraints may also include specific waypoints. For example, a user may indicate that the path should pass through a first location and a second location. The user may further indicate that the path should pass through the first location before passing through the second location. If one or more constraints are placed on the path, the method proceeds to block 735. If no constraints are placed on the path, the method proceeds to block 765. In one embodiment, the possible paths are generated before a user has input constraints. Alternatively, the user may input constraints before the method generates possible paths.

At block 765, possible paths are displayed to a user. The method then proceeds to block 748.

At block 735, the method determines whether there is at least one path that meets all constraints that have been specified by a user. If there is a path that meets all constraints, the method proceeds to block 745. If no path meets all constraints, the method proceeds to block 740.

At block 740, user paths are displayed in an order of importance. Those paths that meet the most constraints are shown first (e.g., at the top of a list), while those paths that meet the fewest constraints are shown last, or not shown at all. In one embodiment, the constraints are each associated with an importance value. The importance value indicates how important it is to a user that a particular constraint be met. Those paths that meet constraints that have a high importance value appear are displayed before those that meet constraints that have a lower importance value. The importance value may be input by the user, or may be preconfigured.

At block 745, paths that meet all constraints are displayed. In one embodiment, paths that do not meet all constraints are also displayed. Paths that do not meet constraints may be displayed as discussed with reference to block 740. The method proceeds to block 748.

At block 748, a user selection of a path is received. At block 750, the method determines whether the user selected a path that failed to meet all constraints. If the user did not choose a path that failed to meet all constraints (e.g., if there were no constraints, or if all constraints were met), the method ends. If the user chose a path that failed to meet all constraints, the method continues to block 755, and the importance value of the constraints that were not met are lowered for future evaluations. The method then ends.

Figure 8:
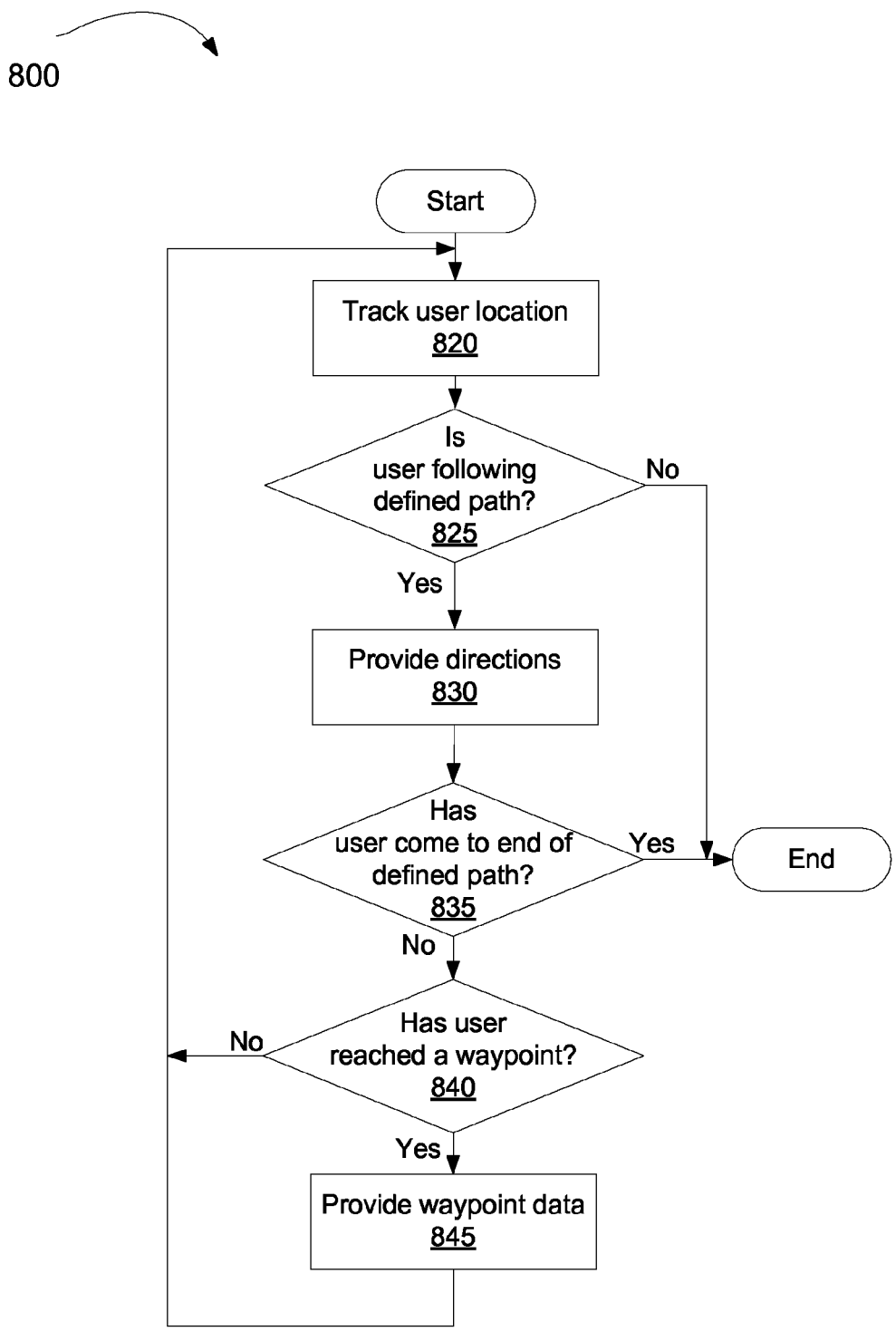
FIG. 8 illustrates a flow diagram for a method of tracking user progress along a defined path, in accordance with one embodiment of the present invention.

FIG. 8 illustrates a flow diagram for a method 800 of tracking user progress along a defined path, in accordance with one embodiment of the present invention. The method may be performed by processing logic that may comprise hardware (e.g., circuitry, dedicated logic, programmable logic, microcode, etc.), software (such as instructions run on a processing device), or a combination thereof. In one embodiment, method 800 is performed by the electronic device 100 of FIG. 1.

Referring to FIG. 8, at block 820, the method tracks user location. User location may be tracked using one or more location based sensors.

At block 825, the method determines whether the user is following a defined path. The defined path may be a track, trail, street, or other physically discernable path. The method may determine that the user is following such a defined path by comparing the user location to a map. The defined path may also be a predetermined path that has been selected by the user. For example, the user may input a destination, and a defined path may be determined that will lead the user from a current location or input starting location to the input destination. Such a predetermined path may not correspond to a physically discernible path such as a trail or street. If the user is following a defined path, the method proceeds to block 830. Otherwise the method ends.

A block 830, the method provides directions to the user. The directions may direct the user, for example, to change direction (e.g., turn right or left) at a specific location. The directions may be provided to the user to keep the user on the defined path. If the user veers from the defined path, the instructions may guide the user back to the defined path.

At block 835, the method determines whether the user as arrived at an end of the defined path. If the user has arrived at the end of the defined path, the method ends. Otherwise, the method proceeds to block 840.

At block 840, the method determines whether the user has reached a waypoint. The waypoint may be a predetermined location that causes the method to perform an action. Examples of actions include providing waypoint data, performing calibration, playing music, etc. If the user has not reached a waypoint, the method returns to block 820. If the user has reached a waypoint, the method proceeds to block 845.

At block 845, the method provides waypoint data. The waypoint data may include current location, user statistics associated with a current run (e.g., average speed, distance traveled, distance remaining in defined path, etc.), and so on. The method then returns to block 820, and continues to track user location.

Figure 9:
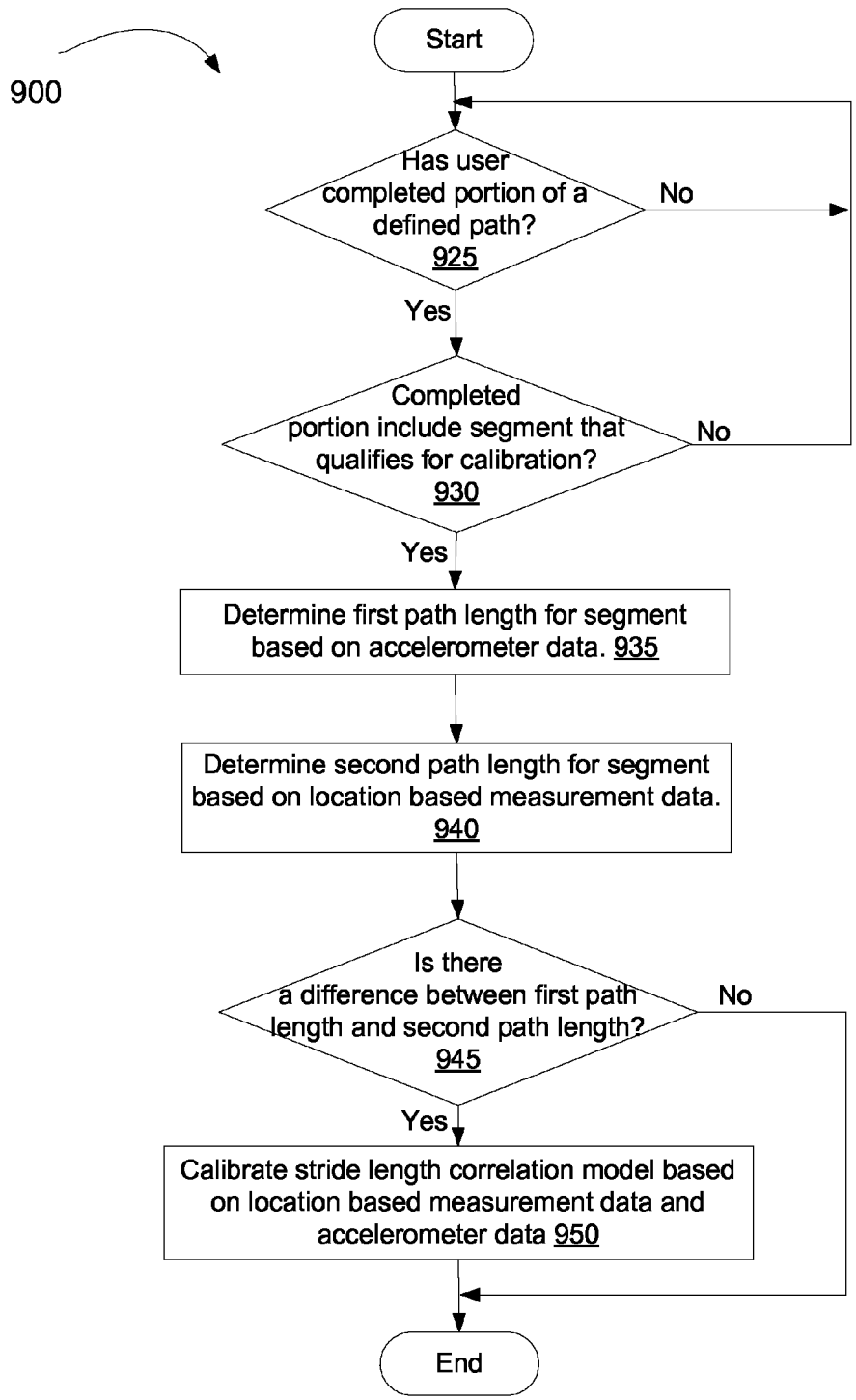
FIG. 9 illustrates a flow diagram for a method of calibrating a stride length correlation model, in accordance with one embodiment of the present invention.

FIG. 9 illustrates a flow diagram for a method 900 of calibrating a stride length correlation model, in accordance with one embodiment of the present invention. In one embodiment, the method calibrates the stride length correlation model during a user activity. In another embodiment, the method calibrates the stride length correlation model after a user activity ends. The method may be performed by processing logic that may comprise hardware (e.g., circuitry, dedicated logic, programmable logic, microcode, etc.), software (such as instructions run on a processing device), or a combination thereof. In one embodiment, method 900 is performed by the electronic device 100 of FIG. 1.

Referring to FIG. 9, at block 925, the method determines whether a user has completed a portion of a defined path. The defined path may have been generated as described with reference to FIG. 7. If the user has not completed a portion of the defined path, the method returns to block 925 and again determines whether the user has completed a portion of the defined path. If the user has completed a portion of the defined path, the method continues to block 930.

At block 930, the method determines whether the completed portion includes a segment that qualifies for calibration. In one embodiment, a segment of the path qualifies for calibration if the user's exact route through the segment of the path can be determined to a high degree of accuracy. Such a determination may be made, for example, by laying GPS sensor data over a map, and determining that a user traveled over a physically discernible path such as a trail. In one embodiment, a segment of the path qualifies for calibration if a user traveled over the segment at a consistent pace (e.g., at a regular cadence). For example, if the user ran over the path at a relatively continuous pace of between 8 and 9 minutes per mile, then the segment may qualify for calibration. In one embodiment, a segment qualifies for calibration if the segment is at a consistent grade or slope (e.g., if the segment is flat). In one embodiment, a segment qualifies for calibration if it meets all of the above mentioned criteria, or alternatively if it meets some of the above mentioned criteria. Other criteria may also be used. If no segments of the completed portion qualify for calibration, the method returns to block 925. If a segment of the completed portion qualifies for calibration, the method proceeds to block 935.

At block 935, a first path length is determined for the qualifying segment based on accelerometer data. At block 940, a second path length is determined for the qualifying segment based on location measurement data (e.g., based on GPS sensor data).

At block 945, the method determines whether there is a difference between the first path length and the second path length. If there is no difference in the path lengths, the method ends. If there is a difference in the path lengths, the method proceeds to block 950.

At block 950, the method calibrates a stride length correlation model based on the location measurement data and the accelerometer data. The stride length correlation model may be calibrated as discussed above with reference to FIG. 1. The method then ends.

Figure 10:
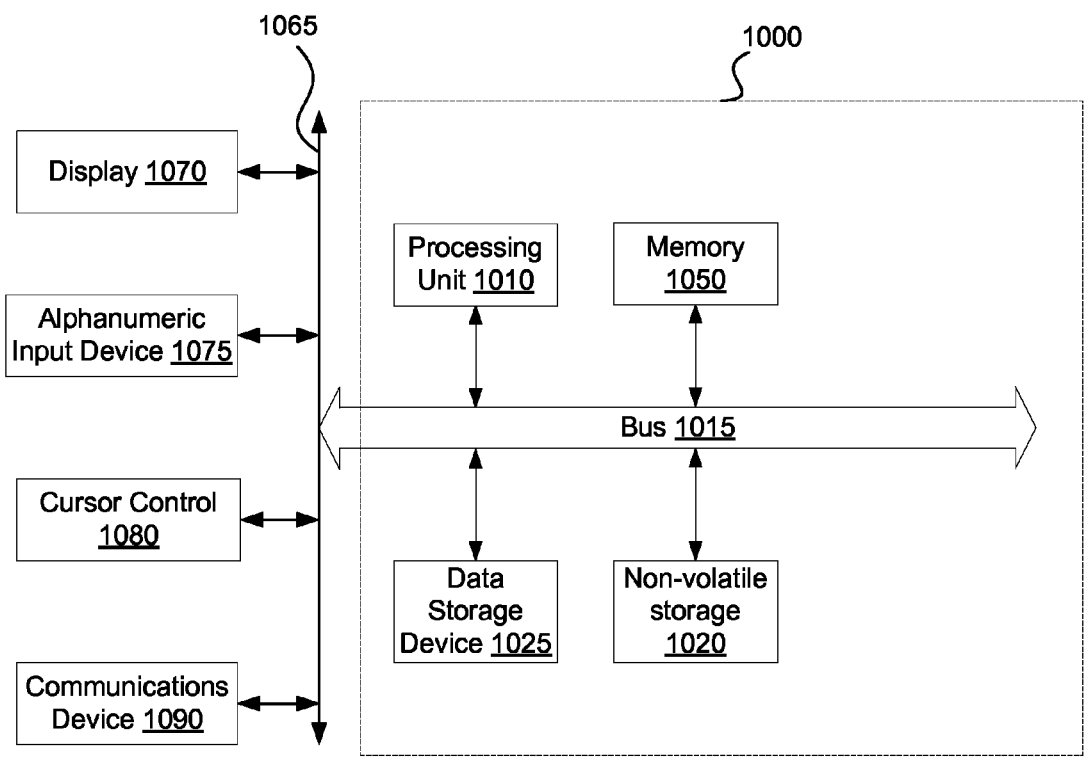
FIG. 10 illustrates a block diagram of a machine in the exemplary form of a computer system, in accordance with one embodiment of the present invention.

FIG. 10 illustrates a block diagram of a machine in the exemplary form of a computer system within which a set of instructions, for causing the machine to perform any one or more of the methodologies discussed herein, may be executed. FIG. 1 is one embodiment of a computer system that may be used with the present invention. It will be apparent to those of ordinary skill in the art, however that other alternative systems of various system architectures may also be used.

Returning to FIG. 10, a data processing system includes a bus or other internal communication means 1015 for communicating information, and a processor 1010 coupled to the bus 1015 for processing information. The system further comprises a random access memory (RAM) or other volatile storage device 1050 (referred to as memory), coupled to bus 1015 for storing information and instructions to be executed by processor 1010. Main memory 1050 also may be used for storing temporary variables or other intermediate information during execution of instructions by processor 1010. The system also comprises a read only memory (ROM) and/or static storage device 1020 coupled to bus 1015 for storing static information and instructions for processor 1010, and a data storage device 1025 such as a magnetic disk or optical disk and its corresponding disk drive. Data storage device 1025 is coupled to bus 1015 for storing information and instructions.

The system may further be coupled to a display device 1070, such as a cathode ray tube (CRT) or a liquid crystal display (LCD) coupled to bus 1015 through bus 1065 for displaying information to a computer user. An alphanumeric input device 1075, including alphanumeric and other keys, may also be coupled to bus 1015 through bus 1065 for communicating information and command selections to processor 1010. An additional user input device is cursor control device 1080, such as a mouse, a trackball, stylus, or cursor direction keys coupled to bus 1015 through bus 1065 for communicating direction information and command selections to processor 1010, and for controlling cursor movement on display device 1070.

Another device, which may optionally be coupled to computer system 1000, is a communication device 1090 for accessing other nodes of a distributed system via a network. The communication device 1090 may include any of a number of commercially available networking peripheral devices such as those used for coupling to an Ethernet, token ring, Internet, or wide area network. The communication device 1090 may further be a null-modem connection, or any other mechanism that provides connectivity between the computer system 1000 and the outside world. Note that any or all of the components of this system illustrated in FIG. 10 and associated hardware may be used in various embodiments of the present invention.

It will be appreciated by those of ordinary skill in the art that any configuration of the system may be used for various purposes according to the particular implementation. The control logic or software implementing the present invention can be stored in main memory 1050, mass storage device 1025, or other storage medium locally or remotely accessible to processor 1010.

It will be apparent to those of ordinary skill in the art that the system, method, and process described herein can be implemented as software stored in main memory 1050 or read only memory 1020 and executed by processor 1010. This control logic or software may also be resident on an article of manufacture comprising a computer readable medium having computer readable program code embodied therein and being readable by the mass storage device 1025 and for causing the processor 1010 to operate in accordance with the methods and teachings herein.

The present invention may also be embodied in a handheld or portable device containing a subset of the computer hardware components described above. For example, the handheld device may be configured to contain only the bus 1015, the processor 1010, and memory 1050 and/or 1025. The handheld device may also be configured to include a set of buttons or input signaling components with which a user may select from a set of available options. The handheld device may also be configured to include an output apparatus such as a liquid crystal display (LCD) or display element matrix for displaying information to a user of the handheld device. Conventional methods may be used to implement such a handheld device. The implementation of the present invention for such a device would be apparent to one of ordinary skill in the art given the disclosure of the present invention as provided herein.

The present invention may also be embodied in a special purpose appliance including a subset of the computer hardware components described above. For example, the appliance may include a processor 1010, a data storage device 1025, a bus 1015, and memory 1050, and only rudimentary communications mechanisms, such as a small touch-screen that permits the user to communicate in a basic manner with the device. In general, the more special-purpose the device is, the fewer of the elements need be present for the device to function. In some devices, communications with the user may be through a touch-based screen, or similar mechanism.

It will be appreciated by those of ordinary skill in the art that any configuration of the system may be used for various purposes according to the particular implementation. The control logic or software implementing the present invention can be stored on any machine-readable medium locally or remotely accessible to processor 1010. A machine-readable medium includes any mechanism for storing or transmitting information in a form readable by a machine (e.g. a computer). For example, a machine readable medium includes read-only memory (ROM), random access memory (RAM), magnetic disk storage media, optical storage media, flash memory devices, electrical, optical, acoustical or other forms of propagated signals (e.g. carrier waves, infrared signals, digital signals, etc.).

The following detailed description of embodiments of the invention makes reference to the accompanying drawings in which like references indicate similar elements, showing by way of illustration specific embodiments of practicing the invention. Description of these embodiments is in sufficient detail to enable those skilled in the art to practice the invention. One skilled in the art understands that other embodiments may be utilized and that logical, mechanical, electrical, functional and other changes may be made without departing from the scope of the present invention. The following detailed description is, therefore, not to be taken in a limiting sense, and the scope of the present invention is defined only by the appended claims.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed is:

1. An mobile device to monitor human activity using multiple sensors comprising:
    a processing unit to provide a first estimation user activity data based on data from a first sensor, the first estimation having a first accuracy estimation, and to provide a second estimation of user activity data based on data from a second sensor, the second estimation having a second accuracy estimation;
    the processor to calculate the user activity statistic based on the first estimation and the second estimation, wherein the calculated user activity statistic is a result of a weighted combination of the first estimation and the second estimation.

2. The mobile device of claim 1, comprising:
    the processing unit comprising a low power processor; and
    a central processor, the central processor to provide other functions.

3. The mobile device of claim 1, further comprising:
    the plurality of sensors including a location sensor and a motion sensor; and
    the calculating logic to verify the calculated user activity based on location information.

4. The mobile device of claim 1, further comprising:
    a transmission system to transmit at least a subset of the data from the plurality of sensors to an external computing device, to generate the user activity statistic.

5. The mobile device of claim 2, wherein the externally calculated user activity statistic includes a reconstruction of an event that started when the user activity was initially detected and ended when the user activity ceased to be detected.

6. The mobile device of claim 1, wherein the user activity statistic is one of a distance traveled, a route traveled, a speed of travel, a current position or a periodic human motion count.

7. The mobile device of claim 1, wherein the first sensor and the second sensor are each one of: an inertial sensor and a location sensor.

8. The mobile device of claim 7, further comprising:
    the calculating logic to verify the calculated user activity based on location information from the location sensor.

9. The mobile device of claim 7, further comprising:
    the calculating logic to verify location information based on accelerations from the inertial sensor and past location information from the location sensor.

10. The mobile device of claim 1, further comprising:
    a central processing unit to receive location information from the location sensor, and when the location information indicates that a user is at a particular location, the central processing unit to automatically perform a preconfigured action.

11. The mobile device of claim 10, wherein the preconfigured action comprises one of: starting or ending a sports training application, starting or ending a run application, providing coaching, logging a workout, initiating another application, and altering an application setting.

12. The mobile device of claim 1, further comprising:
    a microcontroller to receive a starting and an ending point and generate a plurality of possible paths, and further to apply defined constraints on the path, and display the possible paths to the user for selection.

13. The mobile device of claim 12, wherein if the user selects a path that does not meet a defined constraint, the defined constrain is lowered in importance.

14. The mobile device of claim 1, further comprising:
    the processor to identify a path segment suitable for calibration of one of the sensors, and comparing path length for the path segment as measured by the first sensor and the second sensor, and configuring the sensor with a lower accuracy estimation.

15. An electronic device comprising:
    a first sensor to receive a first set data;
    a second sensor to receive a second set data;
    a processor to calculate a first estimation of user activity data based on the first set of data, and a second estimation of the user activity data based on the second set of data;
    the processor to calculate a user activity statistic based on the first estimation and the second estimation, wherein the calculated user activity statistic is a result of a weighted combination of the first estimation and the second estimation.

16. The electronic device of claim 15, wherein the electronic device is one of: a cellular phone, wrist watch, mp3 player, personal digital assistant (PDA), mobile game console, a tablet, and a laptop computer.

17. The electronic device of claim 15, further comprising:
    the first sensor and the second sensor selected from among: an inertial sensor and a location sensor; and
    the first estimation and the second estimation each having an accuracy estimation, wherein the weighted combination utilizes the accuracy estimations.

18. The electronic device of claim 15, further comprising:
    the processor to receive a starting and an ending point and generate a plurality of possible paths, and further to apply defined constraints on the path, and display the possible paths to the user for selection.

19. The electronic device of claim 18, wherein if the user selects a path that does not meet a defined constraint, the defined constrain is lowered in importance.

20. The electronic device of claim 15, further comprising:
    the processor to identify a path segment suitable for calibration of one of the sensors, and comparing path length for the path segment as measured by the first sensor and the second sensor, and configuring the sensor with a lower accuracy estimation.

* * * * *